United States Patent
Harrison et al.

(10) Patent No.: US 8,439,915 B2
(45) Date of Patent: May 14, 2013

(54) APPARATUS AND METHODS FOR MAGNETIC ALTERATION OF ANATOMICAL FEATURES

(75) Inventors: Michael R. Harrison, San Francisco, CA (US); Richard J. Fechter, San Rafael, CA (US); Arthur Moran, San Bruno, CA (US); Darrell Christensen, Petaluma, CA (US)

(73) Assignee: The Regents of the University of California, Oakland, CA (US)

( * ) Notice: Subject to any disclaimer, the term of this patent is extended or adjusted under 35 U.S.C. 154(b) by 1019 days.

(21) Appl. No.: 11/677,700

(22) Filed: Feb. 22, 2007

(65) Prior Publication Data
US 2007/0276378 A1    Nov. 29, 2007

Related U.S. Application Data

(63) Continuation-in-part of application No. 11/431,416, filed on May 9, 2006, now abandoned, which is a continuation-in-part of application No. 10/954,995, filed on Sep. 29, 2004.

(51) Int. Cl.
*A61B 17/70* (2006.01)
(52) U.S. Cl.
USPC ............................................ 606/60; 606/105
(58) Field of Classification Search .................. 606/60, 606/62–68, 90, 105, 246–279, 300–331
See application file for complete search history.

(56) References Cited

U.S. PATENT DOCUMENTS

| | | | |
|---|---|---|---|
| 3,005,458 A | 10/1961 | Brook | |
| 3,745,995 A * | 7/1973 | Kraus | 602/2 |
| 3,890,953 A | 6/1975 | Kraus et al. | |
| 3,915,151 A * | 10/1975 | Kraus | 600/13 |
| 3,939,821 A | 2/1976 | Roth | |
| 3,986,493 A | 10/1976 | Hendren, III | |
| 4,029,091 A * | 6/1977 | von Bezold et al. | 606/33 |
| 4,063,561 A | 12/1977 | McKenna | |
| 4,266,533 A | 5/1981 | Ryaby et al. | |
| 4,340,038 A | 7/1982 | McKean | |
| 4,552,134 A | 11/1985 | Binard | |
| 4,655,100 A * | 4/1987 | Frederick et al. | 74/424.92 |
| 4,896,668 A | 1/1990 | Popoff et al. | |

(Continued)

OTHER PUBLICATIONS

M.R. Harrison et al. "Magnetic Mini-Mover Procedure for Pectus Excavatum: I. DEvelopment, design, and simulations for feasibility and safety", J. Pediatr. Surg. vol. 42, No. 1, pp. 81-85 (2007), discussion pp. 85-86.

(Continued)

*Primary Examiner* — Kevin T Truong
*Assistant Examiner* — Christopher Beccia
(74) *Attorney, Agent, or Firm* — Lumen Patent Firm

(57) ABSTRACT

Systems and methods are disclosed for manipulating an anatomical feature within the body of the patient. An implant such as an internal jackscrew is implanted at the anatomical and has first and second attachment points that secure to spaced-apart locations on the anatomical feature, an internal rotor coupled to the jackscrew, and is configured to drive motion of the jackscrew to manipulate the anatomical feature. The system further includes an external rotor that is magnetically coupled to the internal rotor such that rotation of the external rotor at an exterior location to the patient's body affects a corresponding internal rotation of the internal rotor to manipulate the anatomical feature.

5 Claims, 32 Drawing Sheets

U.S. PATENT DOCUMENTS

| | | | |
|---|---|---|---|
| 4,932,951 A | | 6/1990 | Liboff et al. |
| 5,014,699 A | | 5/1991 | Pollack et al. |
| 5,458,558 A | * | 10/1995 | Liboff et al. ............... 600/13 |
| 5,595,563 A | * | 1/1997 | Moisdon ..................... 600/12 |
| 5,626,579 A | * | 5/1997 | Muschler et al. ............ 606/60 |
| 5,690,656 A | | 11/1997 | Cope et al. |
| 5,704,939 A | * | 1/1998 | Justin ........................ 606/63 |
| 5,984,856 A | * | 11/1999 | Love .......................... 600/15 |
| 6,006,756 A | | 12/1999 | Shadduck |
| 6,022,349 A | * | 2/2000 | McLeod et al. ............. 606/58 |
| 6,024,759 A | | 2/2000 | Nuss et al. |
| 6,099,542 A | | 8/2000 | Cohn et al. |
| 6,200,317 B1 | * | 3/2001 | Aalsma et al. .............. 606/62 |
| 6,292,680 B1 | | 9/2001 | Somogyi et al. |
| 6,306,075 B1 | | 10/2001 | Shadduck |
| 6,352,543 B1 | | 3/2002 | Cole |
| 6,387,096 B1 | * | 5/2002 | Hyde, Jr. .................... 606/60 |
| 6,569,166 B2 | | 5/2003 | Gonzalez |
| 6,652,540 B1 | | 11/2003 | Cole et al. |
| 6,656,194 B1 | | 12/2003 | Gannoe et al. |
| 6,669,709 B1 | | 12/2003 | Cohn et al. |
| 6,719,768 B1 | | 4/2004 | Cole et al. |
| 6,796,984 B2 | * | 9/2004 | Soubeiran .................. 606/300 |
| 6,802,847 B1 | | 10/2004 | Carson et al. |
| 6,849,076 B2 | * | 2/2005 | Blunn et al. ............... 606/105 |
| 6,998,751 B2 | * | 2/2006 | Lopatinsky et al. .......... 310/208 |
| 7,001,402 B2 | | 2/2006 | Yencho |
| 7,135,022 B2 | * | 11/2006 | Kosashvili et al. ........... 606/63 |
| 7,481,841 B2 | * | 1/2009 | Hazebrouck et al. ...... 623/18.12 |
| 7,559,951 B2 | * | 7/2009 | DiSilvestro et al. ....... 623/23.47 |
| 7,753,915 B1 | * | 7/2010 | Eksler et al. ............... 606/105 |
| 7,862,502 B2 | * | 1/2011 | Pool et al. .................. 600/37 |
| 2002/0072758 A1 | | 6/2002 | Reo et al. |
| 2002/0103495 A1 | | 8/2002 | Cole |
| 2003/0144682 A1 | | 7/2003 | Qureshi et al. |
| 2004/0030395 A1 | * | 2/2004 | Blunn et al. ............... 623/18.12 |
| 2004/0116945 A1 | | 6/2004 | Sharkawy et al. |
| 2004/0122334 A1 | | 6/2004 | Yamashiro |
| 2004/0215214 A1 | | 10/2004 | Crews et al. |
| 2005/0021059 A1 | | 1/2005 | Cole et al. |
| 2005/0080439 A1 | | 4/2005 | Carson et al. |
| 2005/0228412 A1 | | 10/2005 | Surti |
| 2005/0234555 A1 | | 10/2005 | Sutton et al. |
| 2006/0009767 A1 | * | 1/2006 | Kiester ....................... 606/61 |
| 2006/0036267 A1 | | 2/2006 | Saadat et al. |
| 2006/0047282 A1 | * | 3/2006 | Gordon ....................... 606/61 |
| 2006/0282106 A1 | | 12/2006 | Cole et al. |
| 2007/0010834 A1 | | 1/2007 | Sharkawy et al. |
| 2007/0156055 A1 | | 7/2007 | Royalty |
| 2007/0250162 A1 | | 10/2007 | Royalty |

OTHER PUBLICATIONS

Leonard, A. Surgical corrective procedure for pectus excavatum and pectus carinatum. http://pectusdeformity.com/, downloaded Jun. 8, 2004, pp. 1-5.

Pittman, T. et al. Cranial vault moulding by the transcutaneous activation of implanted magnets. Pediatr. Neurosurg. 1997, vol. 27, pp. 78-83.

* cited by examiner

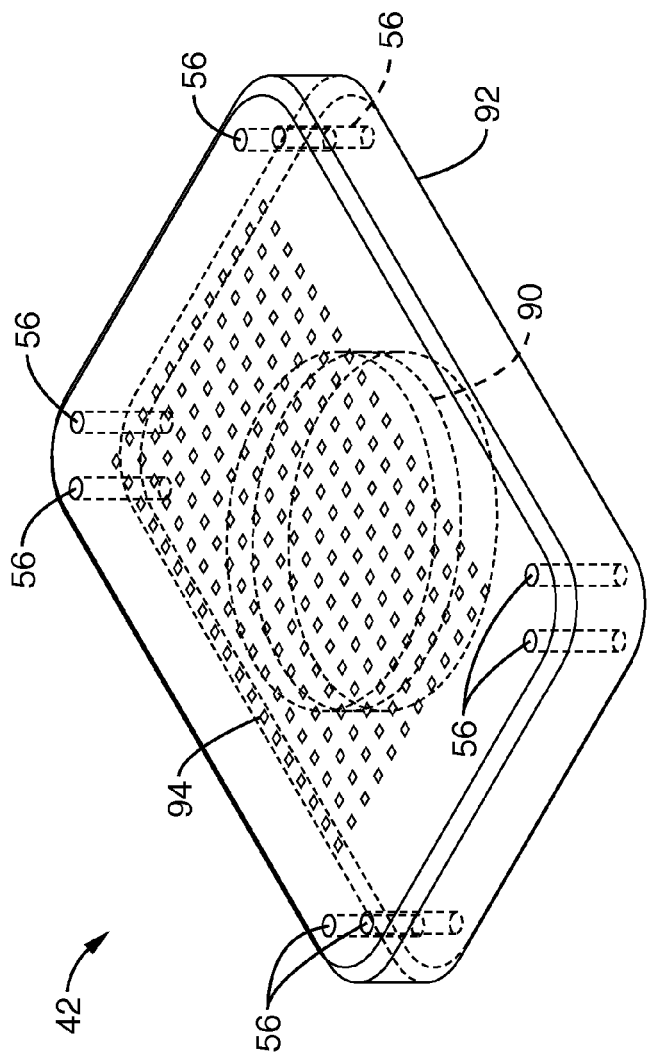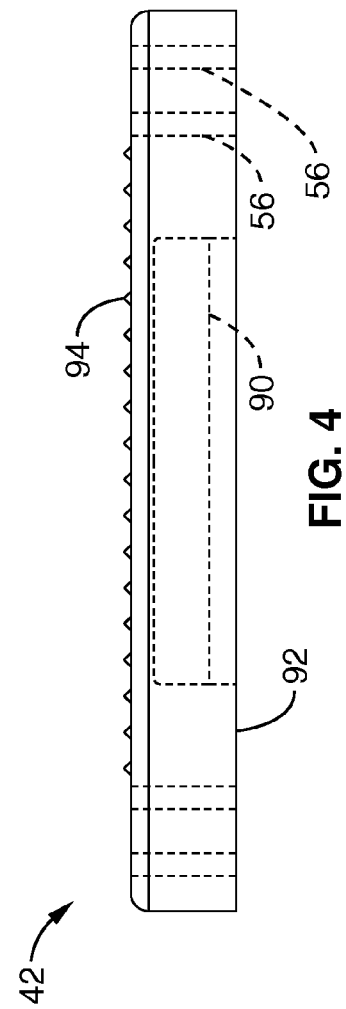

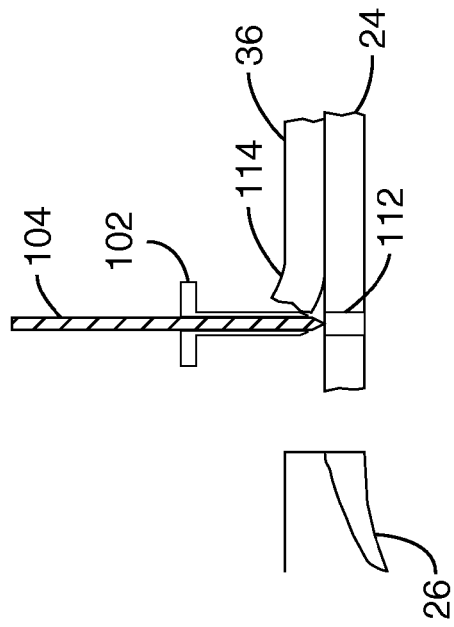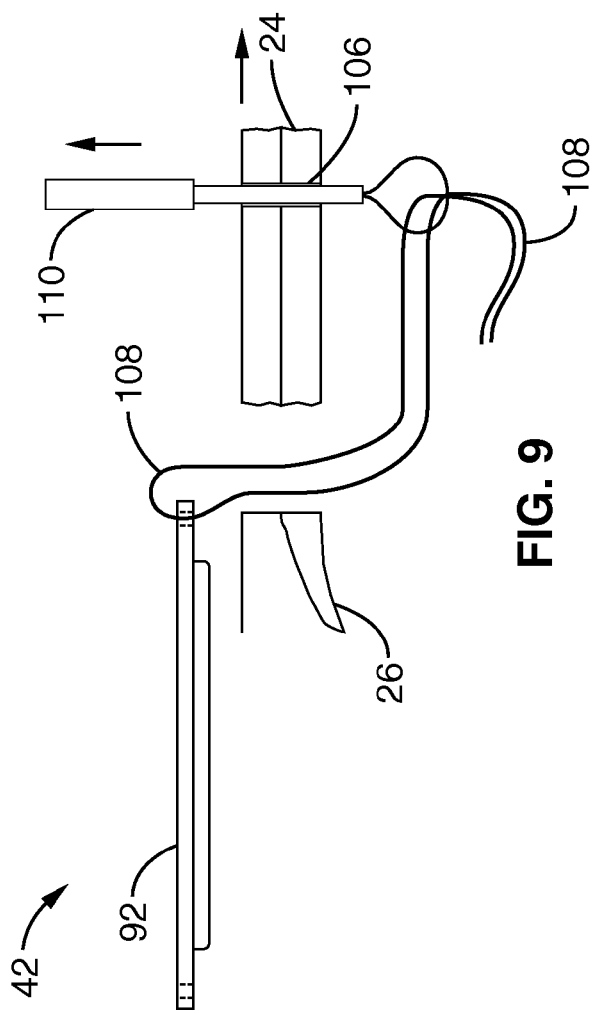

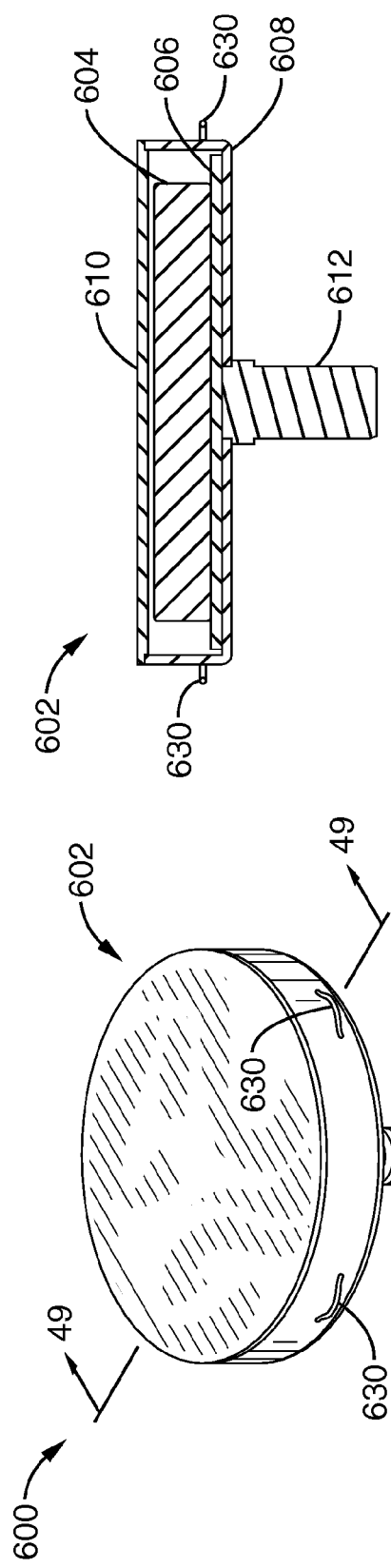
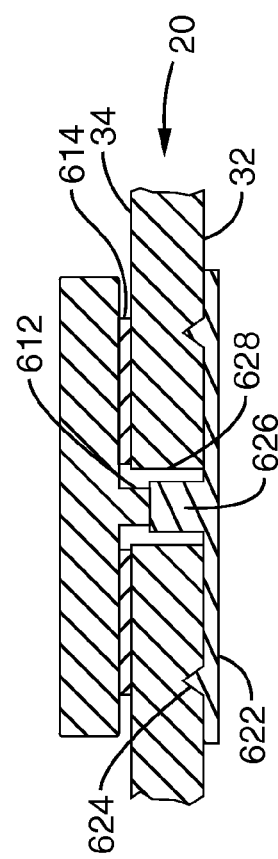
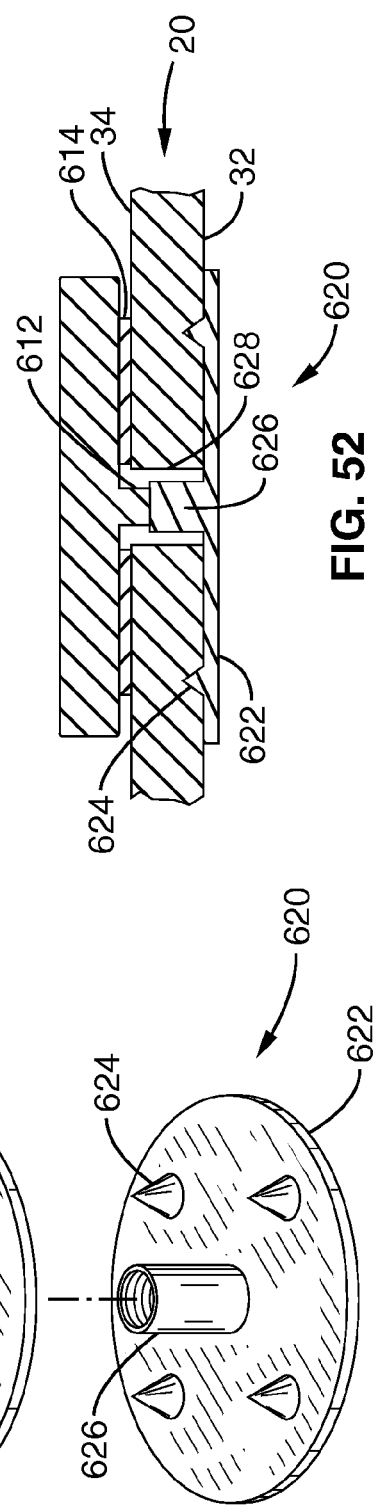
FIG. 51
FIG. 52
FIG. 50

APPARATUS AND METHODS FOR MAGNETIC ALTERATION OF ANATOMICAL FEATURES

CROSS-REFERENCE TO RELATED APPLICATIONS

This application is a continuation-in-part of copending application Ser. No. 11/431,416, filed on May 9, 2006, incorporated herein by reference in its entirety, which is a continuation-in-part of copending application Ser. No. 10/954,995, filed on Sep. 29, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to apparatus and methods for magnetically manipulating body structures and more particularly to performing corrective procedures on a patient via incremental magnetic loading.

2. Description of Related Art

Anatomical deformities occur in the general populous in a number of different forms and from a variety of causes. Examples of skeletal deformities include pectus excavatum, scoliosis, club feet, and numerous forms of skeletal dysplasia. These conditions are treated in a variety of different manners from braces to surgery, with sometimes minimal efficacy.

The defect known as pectus excavatum, or funnel chest, is a congenital anomaly of the anterior chest wall. The excavatum defect is characterized by a deep depression of the sternum, usually involving the lower half or two thirds of the sternum, with the most recessed or deepest area at the junction of the chest and the abdomen. The lower 4-6 costal or rib cartilages dip backward abnormally to increase the deformity or depression and push the sternum posterior or backward toward the spine. Also, in many of these deformities, the sternum is asymmetric or it courses to the right or left in this depression. In many instances, the depression is on the right side.

Pectus excavatum with significant deformity occurs in approximately 1 out of every 2000 births. The deformity may be present at birth but is often noted after several years of age and usually worsens during rapid growth around puberty. Because of the pressure of the sternum and cartilages, defect also pushes the midline structures so that the lungs are compressed from side to side and the heart (right ventricle) is compressed. Severe lesions have a major effect on thoracic volume and pulmonary function but the principal motivation for repair is the deformity itself. It does occur in families and thus, is inherited in many instances. Other problems, especially in the muscle and skeletal system, also may accompany this defect. In approximately ⅕ of the patients, scoliosis is present. The regression or any improvement in this defect rarely occurs because of the fixation of the cartilages and the ligaments. When one takes a deep breath or inspires, the defect is usually accentuated.

Pectus excavatum can be repaired surgically using an open approach in which the malformed costal cartilages are resected and the sternum forcibly held in place with a metal strut. In another approach, described in U.S. Pat. No. 6,024,759, the sternum is forced into a corrected position often under great tension, and held in place with a metal strut. Both can achieve good results but at the cost of considerable morbidity: an operation under general anesthesia followed by a 4-7 day hospital stay required for pain control usually by continuous epidural analgesia. Several more weeks of moderate to severe discomfort are typical and complications from the sternum held forcibly against the metal strut are not infrequent. It is necessary to leave the bar in place for a year or more before it is removed in another procedure. Total cost usually reimbursed by third party payers averages more than $30,000.

The problem with all currently available pectus excavatum surgical repairs is that they attempt to achieve immediate total correction and fixation often under considerable tension. A better approach would be the gradual step-by-step correction of the deformity by applying a smaller force over a longer period of time.

Another skeletal deformity, scoliosis, is a condition in which an individual has an abnormal spine curvature. Generally, some curvature in the neck, upper trunk and lower trunk is normal. However, when there are abnormal side-to-side (lateral) curves in the spinal column, the patient is generally diagnosed as having as scoliosis.

Orthopaedic braces are typically used to prevent further spinal deformity in children with curve magnitudes within the range of 25 to 40 degrees. If these children already have curvatures of these magnitudes and still have a substantial amount of skeletal growth left, then bracing is a viable option. The intent of bracing, however, is to prevent further deformity, and is generally not used to correct the existing curvature or to make the curve disappear.

Surgery is an option used primarily for severe scoliosis (curves greater than 45 degrees) or for curves that do not respond to bracing. The two primary goals for surgery are to stop a curve from progressing during adult life and to diminish spinal deformity.

Although there are different techniques and methods used today for scoliosis surgery, all of them involve fairly invasive procedures with considerable patient morbidity. One frequently performed surgery involves posterior spinal fusion with instrumentation and bone grafting, which is performed through the patient's back. During this surgery, the surgeon attaches a metal rod to each side of the patient's spine by anchors attached to the vertebral bodies. The spine is then fused with a bone graft. The operation usually takes several hours and the patient is typically hospitalized for a week or more. Most patients are not able to return to school or for several weeks after the surgery and cannot perform some pre-operative activities for up to four to six months.

Another surgery option for scoliosis is an anterior approach, wherein the surgery is conducted through the chest walls instead of entering through the patient's back. During this procedure, the surgeon makes incisions in the patient's side, deflates the lung and removes a rib in order to reach the spine. The anterior spinal approach generally has quicker patient rehabilitation, but usually requires bracing for several months after this surgery.

Yet another medical practice in need of improvement is anastomosis of organs, i.e. creating an opening between two normally separate anatomical regions or organs. Anastomosing hollow organs together is a mainstay of surgery: vascular anastomosis, intestinal anastomosis, urinary tract anastomosis are common procedures in the medical practice. Restoring continuity to hollow viscera has been a fertile realm for surgeons, and numerous techniques have evolved in attempt to make these connections work. The most commonly used are suture anastomosis or stapled anastomosis. However, these techniques tend to be highly invasive and result in significant morbidity.

For these reasons, it would be desirable to provide improved apparatus and methods for repositioning bone structures, by applying a corrective force to the bone structure, which could be gradually adjusted much like orthodontic tooth braces.

It would be further desirable to provide a device that applies a corrective force to reposition a body member without a mechanical force that requires piercing of the skin, thereby limiting the specter of infection and wound problems.

In addition, it would be desirable to provide a device for repositioning bones structures having tension-sensing technology to allow measurement of the force applied to correct all types of asymmetric deformities and allow protection of skin against pressure damage.

It would further be desirable to provide improved devices and methods for minimally invasively treating pectus excavatum.

In addition, it would be desirable to provide improved devices and methods for minimally invasively treating scoliosis.

At least some of these objectives will be met with the inventions described hereinafter.

BRIEF SUMMARY OF THE INVENTION

The present invention comprises apparatus and methods for altering the position, orientation, growth or development of body parts and organs by magnetic forces to apply a steady sustained force over time. The invention uses magnetic force fields that may be used to correct a number of anatomic deformities, including, but not limited to: pectum excavetum, pectus carinatum, scoliosis, club feet, cranial/facial anomalies or defects, skeletal dysplasias, cartilaginous deformities/dysphasia, and joint deformities/dysphasia. The invention may also be used to incrementally lengthen bone or apply bone compression to promote healing.

An aspect of the invention is an apparatus for incrementally manipulating an internal body member of a patient. In one embodiment, the apparatus comprises magnetic implant adapted to be received on a location of the body member, a platform external to the patient, and a magnetic member coupled to the platform, wherein the magnetic member generates a magnetic force between the implant and the platform to incrementally manipulate the body member. The implant and external magnetic member preferably comprise a rare earth magnet or array of rare earth magnets, and are configured to generate an attractive or repulsive force between the implant and the platform to reposition, reorient, deform, or lengthen the body member.

In one aspect of the invention, the implant is adapted to be received on a location of the sternum to treat pectus excavatum. In this configuration the platform comprises a chest plate adapted to be positioned exterior to the patient's chest. The magnetic member is coupled to the chest plate to generate an attractive force between the implant and the chest plate to incrementally reposition the sternum.

The implant is preferably adapted to be received on a posterior surface on the sternum. The implant generally comprises an internal magnet and a casing to enclose the internal magnet. The casing may be made from any rigid biocompatible material capable of withstanding the forces of the magnet without significant deformation, such as high-grade medical epoxy or similar material used in the art.

In a preferred embodiment, the implant is attached to the sternum using a plurality of sutures, wherein the sutures are looped through a plurality of holes in the implant casing and around the sternum to attach the implant to the posterior surface of the sternum.

In one embodiment, the platform chest plate generally has a concave inner surface to allow the sternum to deform outwardly from the chest. The platform may also have an adjustable stage coupled to the chest plate, wherein the magnetic member is mounted on the stage. A plurality of adjustment members may be coupled to the stage to adjust the orientation and position of the magnetic member with the implant.

In another embodiment of the invention, a plurality of sensors and a strain gauge may be coupled to the chest plate, with the strain gauge measuring the force applied to one or more locations on the platform.

In most cases the attractive force of the magnets support the chest plate to the patient's chest. However, a chest strap may also be used to support the chest plate to the patient's chest.

In another aspect of the invention, the implant is adapted to be received on a location of a vertebra of the patient's spine to treat scoliosis or other spinal disorders. In this configuration, the platform comprises a support adapted to be positioned exterior to the patient's torso. Generally, the magnetic member is coupled to the support such that the magnetic member generates a magnetic force between the implant and the plate to incrementally reposition the spine. The magnetic member and the implant may be configured to generate an attractive or repulsive force between the implant and the magnetic member.

Where the patient has an abnormal curvature of the spine, the implant is preferably configured to be received on a vertebrae located at an apex of the abnormal curvature. The support may be positioned such that the magnetic force incrementally repositions the spine to remove the abnormal curvature. The implant and the magnetic member may also be configured to impart a torsional force on the vertebrae to incrementally reorient the spine.

In one embodiment, a bone screw is threaded into the vertebrae to rigidly couple the implant to the vertebrae.

According to another aspect of the invention, a method for incrementally repositioning an internal body member of a patient comprises installing a magnetically responsive implant to a location on the internal body member; positioning a platform exterior the patient to generate a magnetic field, the magnetic field effecting an magnetic force between the implant and the platform, and manipulating the body member to a first state as a result of the generated magnetic force.

In a preferred embodiment, the method also includes adjusting the magnetic field to one or more intermediate settings, manipulating the body member to one or more intermediate state as a result of the attractive force generated by the one or more adjusted magnetic field settings, adjusting the magnetic field to a final setting; and manipulating the body member to a final state as a result of the attractive force generated by the final magnetic field setting.

The step of generating a magnetic field may comprise generating an attractive or repulsive force between the implant and the platform. The body member may be manipulated by repositioning the body member to a first position, deforming the body member to a first shape, or lengthening the body member to a first length. Repositioning the sternum may comprise deforming one or more cartilages connected to the sternum as a result of the attractive force, or deforming the shape of the sternum as a result of the attractive force.

In one aspect of the invention, manipulating a body member comprises manipulating the patient's sternum. In such a configuration, installing a magnetically responsive implant comprises attaching an internal magnet to a posterior location on the sternum. Positioning a platform is achieved by manipulating a stage housing an external magnet, the stage being coupled to a chest plate. A plurality of adjustment members may be used to adjust the position and orientation of the external magnet with respect to the internal magnet, thereby effecting the magnitude and direction of the magnetic force between the platform and the implant.

In one aspect of the invention, manipulating a body member comprises manipulating a vertebra of the patient. In such a configuration, installing a magnetically responsive implant comprises attaching an internal magnet to a location on the vertebrae. The vertebrae may be manipulated by adjusting the magnetic field between the implant and the platform to incrementally reposition the spine. The magnetic field may be adjusted to generate an attractive or repulsive force between the implant and the platform to incrementally reposition the spine. Where the spine has an abnormal curvature, the implant is installed on a vertebrae located at an apex of the abnormal curvature. In such a configuration the vertebrae may be manipulated to incrementally reposition the spine to remove the abnormal curvature. A torsional force may also be imparted on the vertebrae to incrementally reorient the spine.

In a preferred embodiment, installing the implant comprises boring a hole in a pedicle of the vertebrae, and threading a pedicle screw into the pedicle, the pedicle screw configured to rigidly couple the implant to the vertebrae.

In another aspect of the invention method is disclosed for performing a pectus excavatum procedure on a patient having a deformed sternum. The method comprises attaching a magnetically responsive implant to a location on the sternum, and positioning a chest plate exterior the patient's chest to generate a magnetic field, wherein the magnetic field effects an attractive force between the implant and the chest plate. The implant generally comprises a first magnet housed in a biocompatible casing.

The first magnet may be attached to a posterior surface on the sternum by incising a section of the patient's skin over the patient's sternum, separating the xiphoid process from the sternum, dissecting under the sternum and securing the first magnet to the posterior surface of the sternum. One method for securing the first magnet to the sternum comprises drilling a plurality of holes from an anterior location on the sternum to a posterior location on the sternum, and looping a plurality of sutures through the holes in the sternum and through a plurality of holes in the casing housing the first magnet.

According to yet another aspect of the invention, a method for incrementally repositioning a patient's sternum is disclosed. The method comprises installing a magnetically responsive implant to a location on the sternum, positioning a chest plate exterior the patient's chest to generate a magnetic field, wherein the magnetic field effects an attractive force between the implant and the chest plate, repositioning the patient's sternum to a first position as a result of the generated magnetic force, manipulating the magnetic field to one or more intermediate settings, repositioning the patient's sternum to one or more intermediate positions as a result of the attractive force generated by the one or more manipulated magnetic field settings, manipulating the magnetic field to a final setting, and repositioning the patient's sternum to a final position as a result of the attractive force generated by the final magnetic field setting.

According to a further aspect of the invention, an apparatus for incrementally manipulating an internal body member of a patient comprises a magnetically responsive implant adapted to be received on a location of the body member, the implant responsive to a magnetic field, and means for generating an attractive force between the implant and a platform external to the patient to manipulate the body member. The device may further comprise means for adjusting the magnitude and direction of the magnetic force applied between the platform and the implant. The device also has means for securing the implant to a location on the body member.

In a preferred embodiment, the apparatus has a means for detecting the force applied to the platform at a plurality of locations on the platform, such as a strain gauge. The strain gauge may also configured to measure the force at a plurality of locations on the platform.

According to yet another aspect of the invention, a method for incrementally repositioning an internal body member of a patient comprises installing a magnetically responsive implant to a location on the internal body member, positioning a platform exterior the patient to generate a magnetic field, the magnetic field effecting a magnetic force between the implant and the platform, measuring the magnetic force between the implant and the platform; adjusting the platform to tune the magnetic force applied between the implant and the platform; and manipulating the body member to a first state as a result of the generated magnetic force.

In an alternative embodiment of the present invention, an apparatus for manipulating one or more internal body members is disclosed. The apparatus comprises a first elongate member having a driving end and a receiving end, wherein the receiving end of the first member having a recess extending toward the driving end. The apparatus also has a second elongate member having a driving end and a receiving end, the receiving end of the second member having a recess extending toward the driving end. The second member is sized such that the receiving end of the second member is slideably received within the receiving end of the first member. The apparatus further comprises a first magnet coupled to the first member, and a second magnet coupled to the second member, wherein the first and second magnets are configured to repel each other such that an outward magnetic force is generated to the driving ends of the first and second members. The first and second magnets may be positioned within the recesses to change the magnitude of the force generated between the first and second magnets. The first and second magnets may also be configured such that rotation of the first magnet with respect to the second magnet changes the magnitude of the force generated between the first and second magnets.

In one embodiment, the implant is adapted to be received on an anterior surface on the sternum. Preferably, the implant fastens to a retaining plate on a posterior surface of the sternum. For example the implant may be configured to thread into a receiving post through a hole drilled in the sternum.

In yet another embodiment, the external magnet is configured to be suspended from the chest plate via a housing. The housing may be selected from a series of housings having different heights configured to retain the magnet at a specified distance from the internal magnet.

In a further embodiment, a sensor is disposed between the chest plate and the external magnet; wherein the sensor is configured to measure the attractive force between the implant and the chest plate.

According to another aspect of the invention, an apparatus for intermittently delivering a force to a body member to incrementally manipulate the body member comprises an implant adapted to be received on a location of the body member, the implant responsive to a magnetic field, a platform external to the patient, and a magnetic member coupled to the platform, wherein the magnetic member generates a magnetic force between the implant and the platform to incrementally manipulate the body member, the magnetic member and the implant configured such that rotation of the magnetic member varies the magnetic force between the implant and the platform.

Yet another aspect is a method for auto-anastomosing a region of the body. The method includes delivering a first magnetic member to a first location in the body adjacent the region, and locating a second magnetic member adjacent the region opposite from the first magnetic member, such that the region is disposed in between the first magnetic member and the second magnetic member. An attractive force is generated between the first magnetic member and the second magnetic member to compress tissue in the region between the first magnetic member and the second magnetic member. This compressive force results in necrosis of the tissue in the region between the first and second magnetic members such that the tissue surrounding the necrosed tissue heals together to form an anastomosis.

In a preferred embodiment of the present aspect, the method further includes removing the necrosed tissue and the first and second magnetic members from the region. Often, the necrosed tissue and the first and second magnetic members are removed from the region via flow of natural bodily functions. If need be, the first and second magnetic members may also be retrieved from a location at or near the region.

In another embodiment, the region comprises tissue occupied by first and second internal viscera segments in the body. The first magnetic member is delivered into the first viscera segment, and the second magnetic member is correspondingly delivered to the second viscera segment at a location in proximity to the first magnet to generate a compressive force on the tissue in between first and second viscera segments. Subsequently, the anastomosed region creates a fistula between the first and second viscera segments.

In some embodiments, the first viscera segment is located in a first viscera, and the second viscera segment is located in a location in a second viscera in proximity to the first viscera. Alternatively, the first viscera segment and second viscera segment are separate sections of the same viscera.

The viscera may be any hollow organ or lumen where anastomosis is desired. In a preferred embodiment, the method is performed on an organ or lumen, or plurality of organs or lumens, in the gastrointestinal or urinary tracts, such as the small intestines, stomach, colon, ureters, renal pelvis, bladder, urethra, etc.

In another embodiment, the treated region comprises tissue occupied by a visceral wall and surrounding tissue between the visceral wall and an external surface on the body. The first magnetic member is delivered to the visceral wall, and the second magnetic member is located adjacent the external surface in proximity to the first magnetic member to create a stoma between the internal visceral wall and the external surface.

Another aspect of the invention is a system for auto-anastomosing a region of the body. The system includes a first magnetic member configured to be delivered to a location in the body adjacent the region, and a second magnetic member configured to be located adjacent the region opposite from the first magnetic member such that the region is disposed in between the first magnetic member and the second magnetic member. The first and second magnetic members are configured to generate an attractive force to compress tissue in the region between them. The tissue in the region necroses as a result of the compressive force such that tissue surrounding the necrosed tissue heals together to form an anastomosis.

The system may further include a catheter that is configured to deliver the first magnetic member to the location adjacent the region and release the first magnetic member at the location.

In a preferred embodiment, the first magnetic member comprises a biocompatible casing, such as a titanium enclosure, or epoxy coating.

Yet another aspect is an apparatus for auto-anastomosing a region of the body comprising a first visceral wall. The apparatus comprises a first magnetic member configured to be delivered to a first location at the first visceral wall, the first location being adjacent the region, and a second magnetic member configured to be positioned at a second location adjacent the region opposite from the first magnetic member such that the region is disposed in between the first magnetic member and the second magnetic member. The first and second magnetic members are configured to generate an attractive force to compress and necrose the tissue in the region between them, such that tissue surrounding the necrosed tissue heals together to form a fistula from the first location to the second location.

In a preferred embodiment, the region further comprises tissue occupied by a second internal viscera wall in the body, and wherein the second magnetic member is configured to be delivered to the second visceral wall at a the second location to generate a compressive force on the tissue in the tissue in between first and second visceral walls.

Alternatively, the region comprises abdominal tissue in between the visceral wall and an external surface on the body, wherein the second magnetic member is configured to be positioned adjacent the external surface at the second location such that the fistula creates a stoma connecting the internal visceral wall to the external surface.

Additionally, the apparatus may also have an intermediate magnetic member configured to be positioned in the abdominal tissue between the first magnetic member and the second magnetic member to generate a compressive force between it and both the first magnetic member and the second magnetic member.

In one embodiment, the apparatus comprises first and second magnets have mating curvilinear surfaces configured to generate a non-uniform compressive force distribution across the surface of the first and second magnets. The first magnetic member may comprise a concave spherical surface having a first radius, and the second magnetic member has a convex spherical surface having a second radius, wherein the first radius is larger than the second radius such that a non-uniform compressive force is distributed across said region of compressed tissue. The concave spherical surface and the convex spherical surface may be configured such the compressive force increases radially inward from the periphery of said surfaces.

In a preferred mode of the present embodiment, the compressive force is configured to necrose tissue radially inward with respect to the surfaces, and the compressive force at the periphery is configured to promote growth and fuse the tissue at the periphery.

Another aspect of the invention is an apparatus for incrementally adjusting the length between a first body segment and a second body segment within the body of a patient. The apparatus comprises an implant configured to be installed within the body. The implant has a first member with a first attachment point for fixation to the first body segment, and a second member with a second attachment point for fixation to the second body segment. The first member is moveably coupled to the second member to allow linear motion of the first member with respect to the second member. The apparatus further includes a first magnetic rotor coupled to the first and second members, such that rotation of the first rotor drives motion of the second member with respect to the first member. The first rotor is rotationally responsive to a magnetic field applied by a second magnetic rotor external to the patient's body, such that the first rotor rotates in response to manipulation of the second rotor to incrementally adjust the length between the first attachment point and the second attachment point.

The first member may be coupled to the second member via a worm drive, wherein rotation of the first rotor drives motion of the worm drive. The apparatus may further comprise a gear reduction unit coupled between the first rotor and the worm drive to facilitate a high ratio gear reduction of the rotation of the first rotor to the worm drive.

In one embodiment, the first and second magnetic rotors comprise radially polarized magnets, such that rotation of the second magnet affects a corresponding rotation of the first magnet. The second rotor may be coupled to a radial motor to drive rotation of the second rotor. The radial motor may have a control to vary the speed and directionality of the second rotor rotation to allow micro-motion control of the distance between the first and second attachment points.

The apparatus may also comprise a force measurement transducer coupled to the first or second members, wherein the transducer is configured to measure a force applied to the first and second attachment points by the implant.

In another embodiment, a biasing member is coupled to the first or second members, wherein the biasing member is configured to absorb loading between the first and second members.

In one embodiment, the first attachment point is configured to secure to a first vertebra and the second attachment point is configured to attach to a second vertebra, wherein the implant is configured to distract the first vertebra from the second vertebra.

Another aspect is a method for manipulating first and second body segments within the body of a patient. The method includes inserting an implant at a location within the body, securing a first attachment point of the implant point to the first body segment, securing a second attachment point of the implant point to the second body segment, and magnetically driving an internal coupling connected to the implant at a location inside the patient's body by driving an external coupling outside the patient's body. The internal coupling is responsive to motion of the external coupling. Finally, the distance between the first and second attachment points may be adjusted as a result of motion of the internal coupling.

In one embodiment, adjusting the distance between the first and second attachment allows incremental manipulation of the first body segment with respect to the second body segment.

In another embodiment, a first member comprising the first attachment point is moveably coupled to a second member comprising the second attachment point, wherein adjusting the distance between the first and second attachment points comprises linearly translating the first member with respect to the second member.

In one embodiment, the internal coupling and external coupling comprise magnetically charged rotors so that magnetically driving the internal coupling comprises rotating the external rotor to affect a corresponding rotation of the internal rotor.

In another embodiment, the first member is coupled to the second member via a worm drive, wherein the worm drive transforms the rotational motion of the internal rotor into linear adjustment of the distance between the first and second attachment points.

The method may also include reducing the gear ratio between the internal rotor and the worm drive. The gear reduction allows a smaller input force on the internal rotor to drive a larger output force between the first and second attachment points. The speed and directionality of the second rotor rotation may be controlled to affect micro-motion control of the distance between the first and second attachment points.

The method may further include measuring a force applied to the first and second body segments by the implant, and wirelessly transmitting said force measurement to a location external to the patient.

The method may also comprise preloading the first and second attachment points by coupling a biasing member to the first or second members to absorb a load generated between the first and second members.

A further aspect is a system for manipulating an anatomical feature within the body of the patient. The system includes an internal jackscrew configured to be implanted at the anatomical feature inside the patient. The jackscrew has first and second attachment points configured to secure to spaced-apart locations on the anatomical feature. An internal rotor coupled to the jackscrew to drive motion of the jackscrew to manipulate the anatomical feature. An external rotor may be positioned to be magnetically coupled to the internal rotor such that rotation of the external rotor at an exterior location to the patient's body affects a corresponding internal rotation of the internal rotor to manipulate the anatomical feature.

In one embodiment, the anatomical feature comprises the patient's spine, wherein the first attachment point is configured to secure to a first vertebra and the second attachment point is configured to attach to a second vertebra of the spine, and wherein the implant is configured to incrementally distract the spine.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL
VIEWS OF THE DRAWING(S)

The invention will be more fully understood by reference to the following drawings which are for illustrative purposes only, and where like reference numbers denote like elements:

FIG. 3 shows an embodiment of the implant of the present invention.

FIG. 4 is a side view of the implant of FIG. 3.

Figure 5:
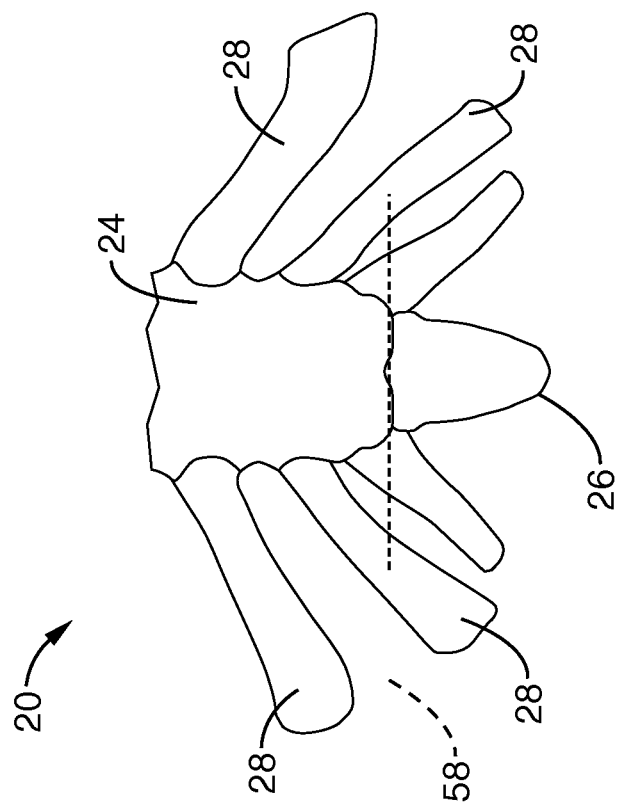

FIG. 5. is a schematic view of a sternum.

Figure 6:
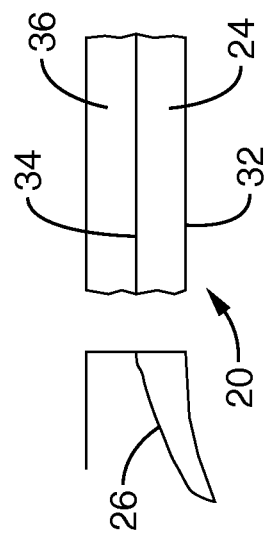

FIG. 6. is a cross-sectional view of a sternum with the xiphoid separated from the sternum body.

Figure 7:
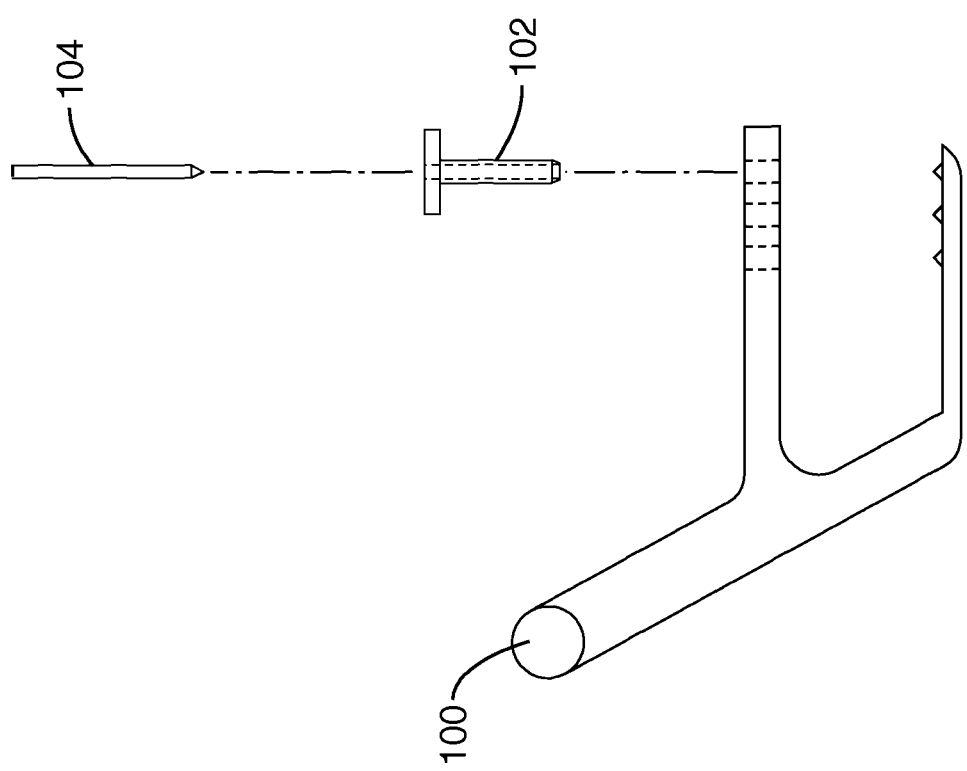

FIG. 7 is an implant drill guide according to the present invention.

Figure 8:
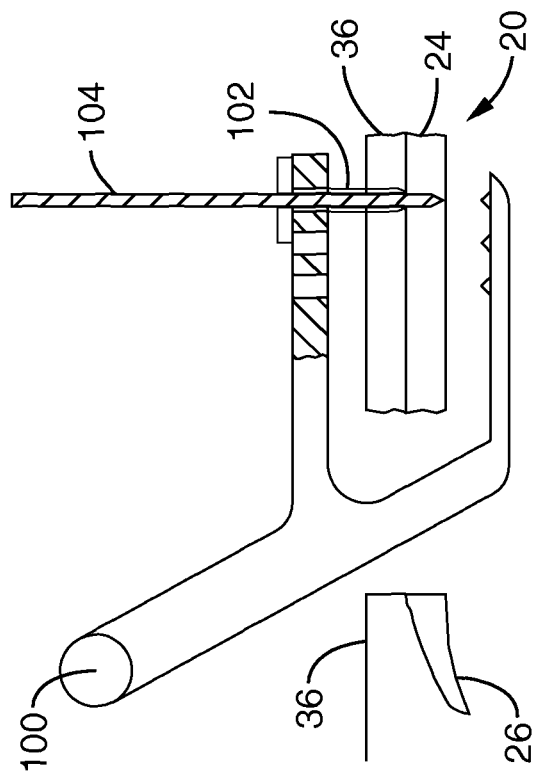

FIG. 8 shows the drill guide of FIG. 7 installed over the sternum.

FIG. 9 illustrates a preferred method for installing a portion of the implant to the posterior surface of the sternum.

FIG. 10 illustrates a portion of the drill guide of FIG. 7 positioned over a second location on the sternum.

Figure 11:
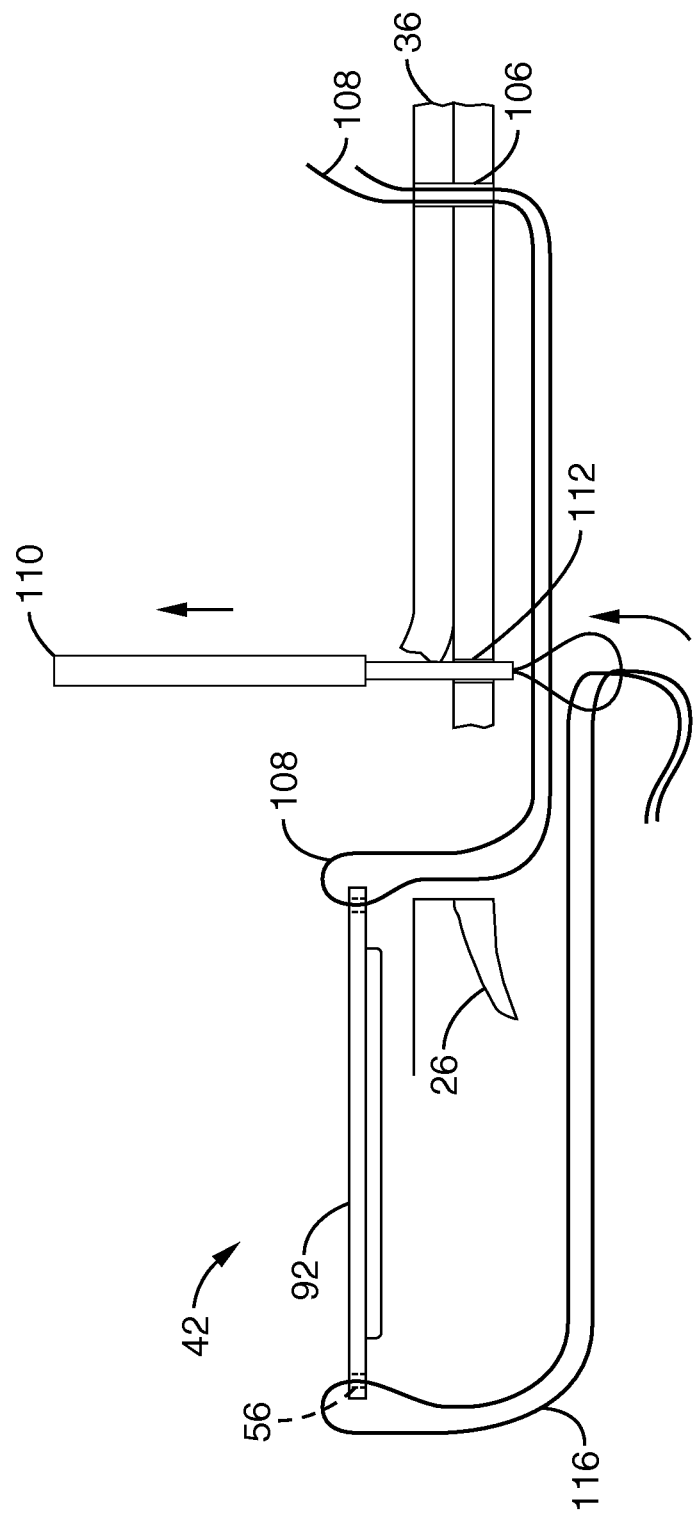

FIG. 11 illustrates a preferred method for installing a second portion of the implant to the posterior surface of the sternum.

Figure 12:
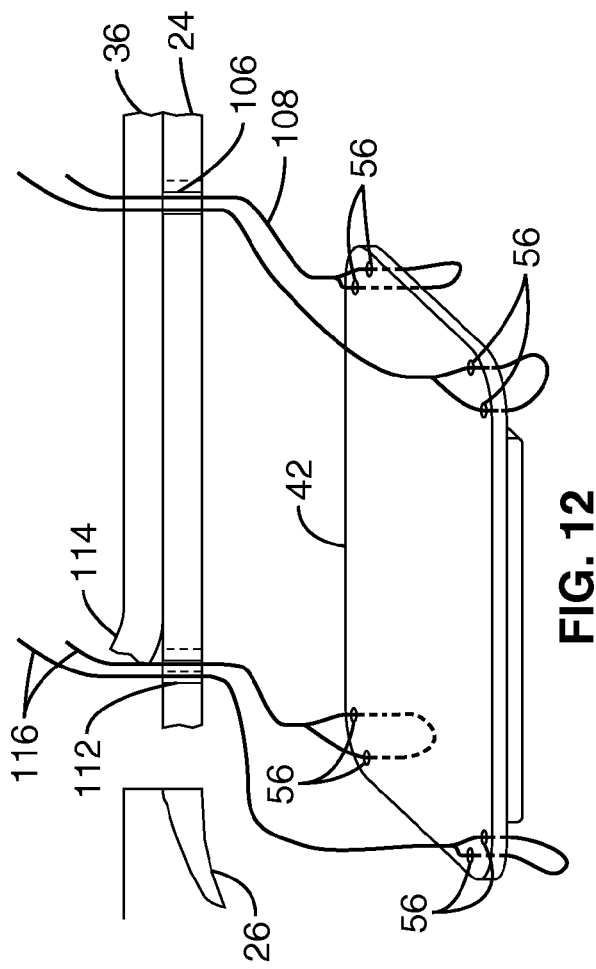

FIG. 12 is another view of the method of FIG. 11.

Figure 13:
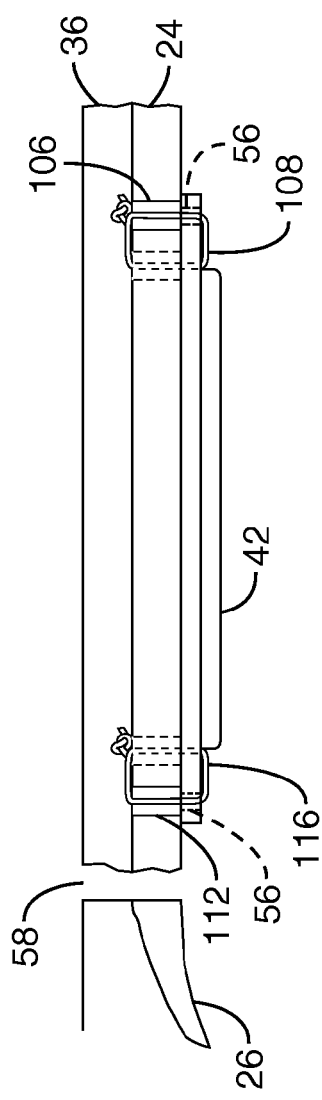

FIG. 13 shows the implant according to the present invention installed on the posterior surface of the sternum.

Figure 14:
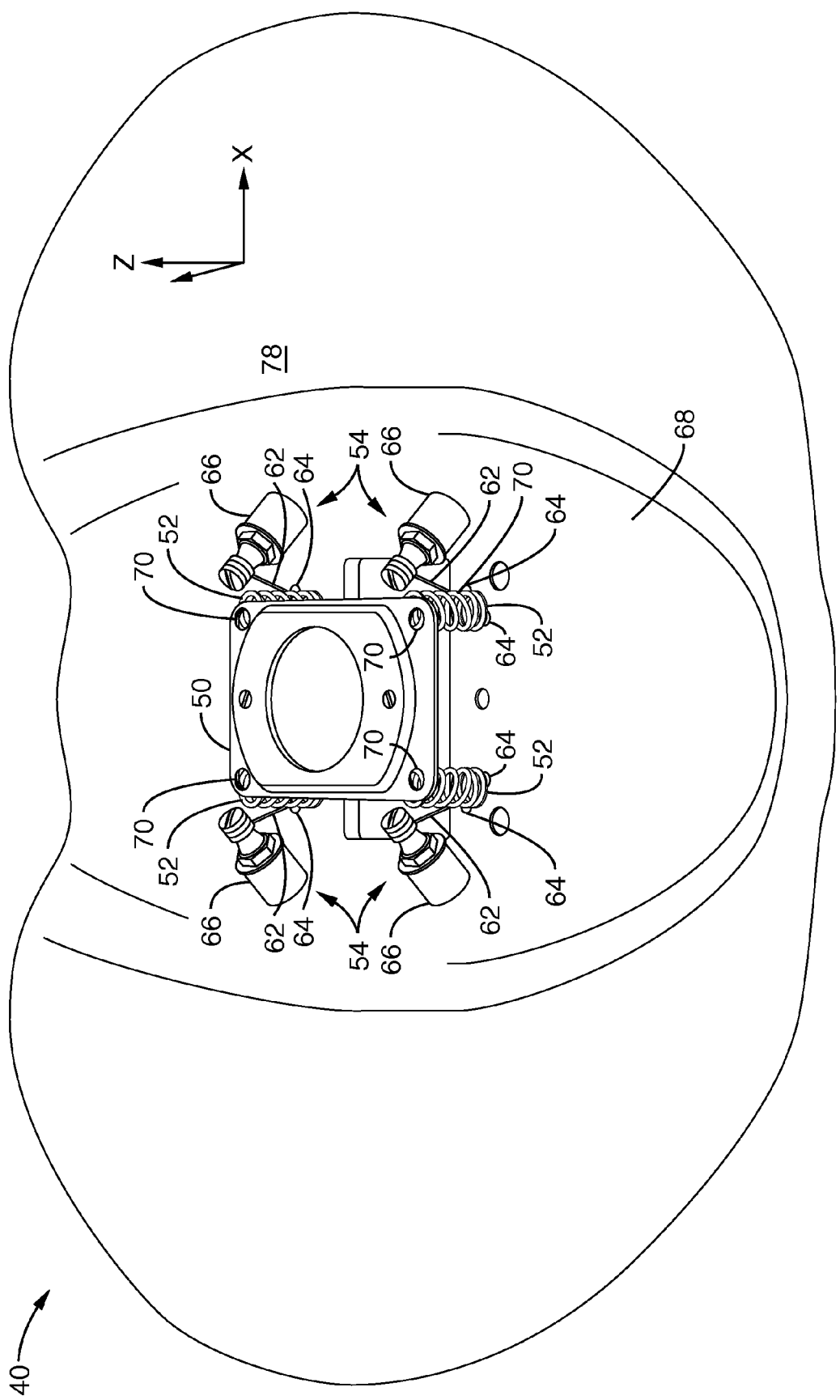

FIG. 14 is a view of the underside of an embodiment of the platform according to the present invention.

Figure 15:
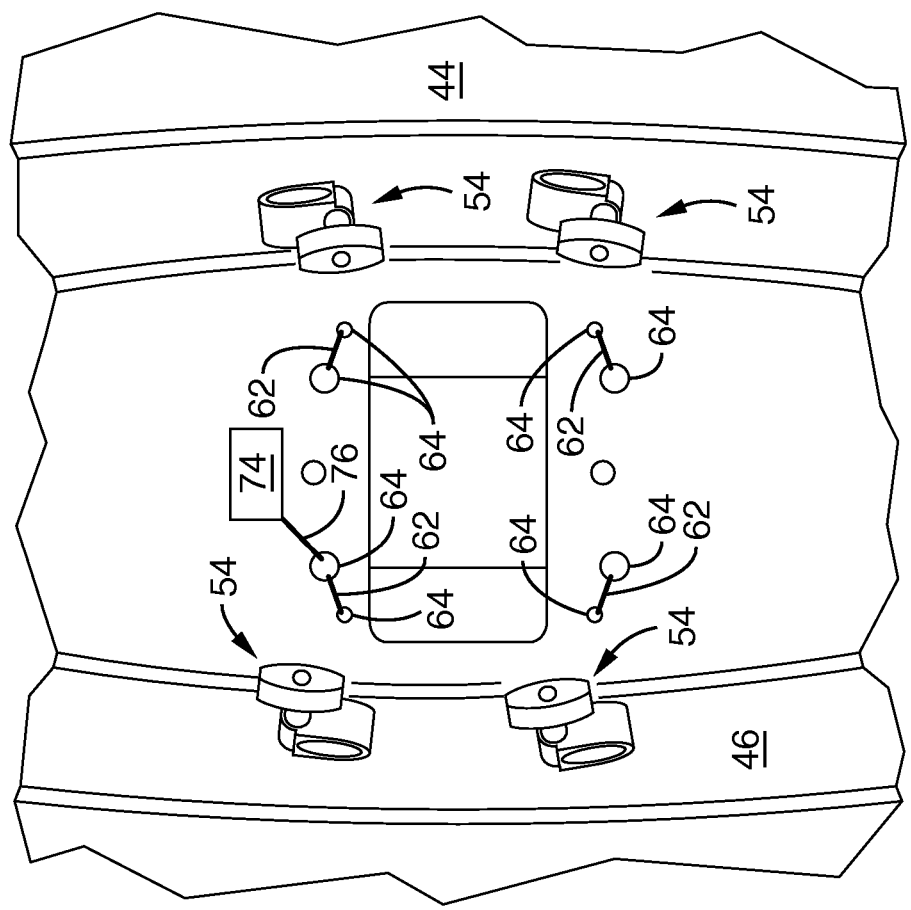

FIG. 15 is a view of the top of the platform of FIG. 14.

Figure 16:
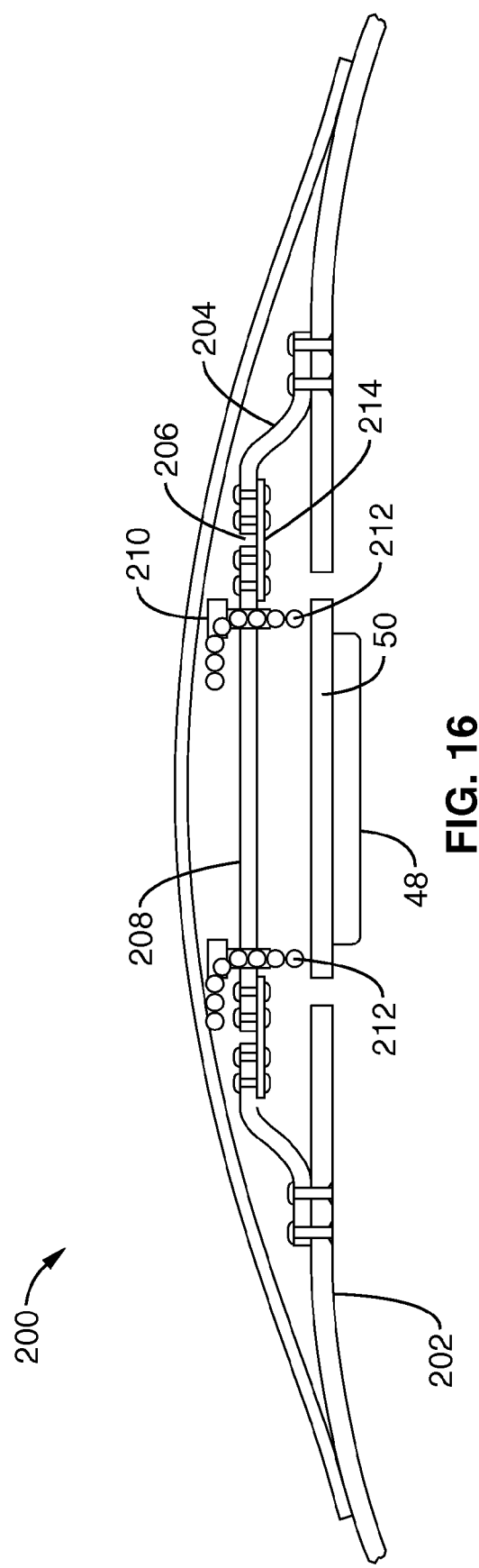

FIG. 16 is a side view of another embodiment of the platform of the present invention.

Figure 17:
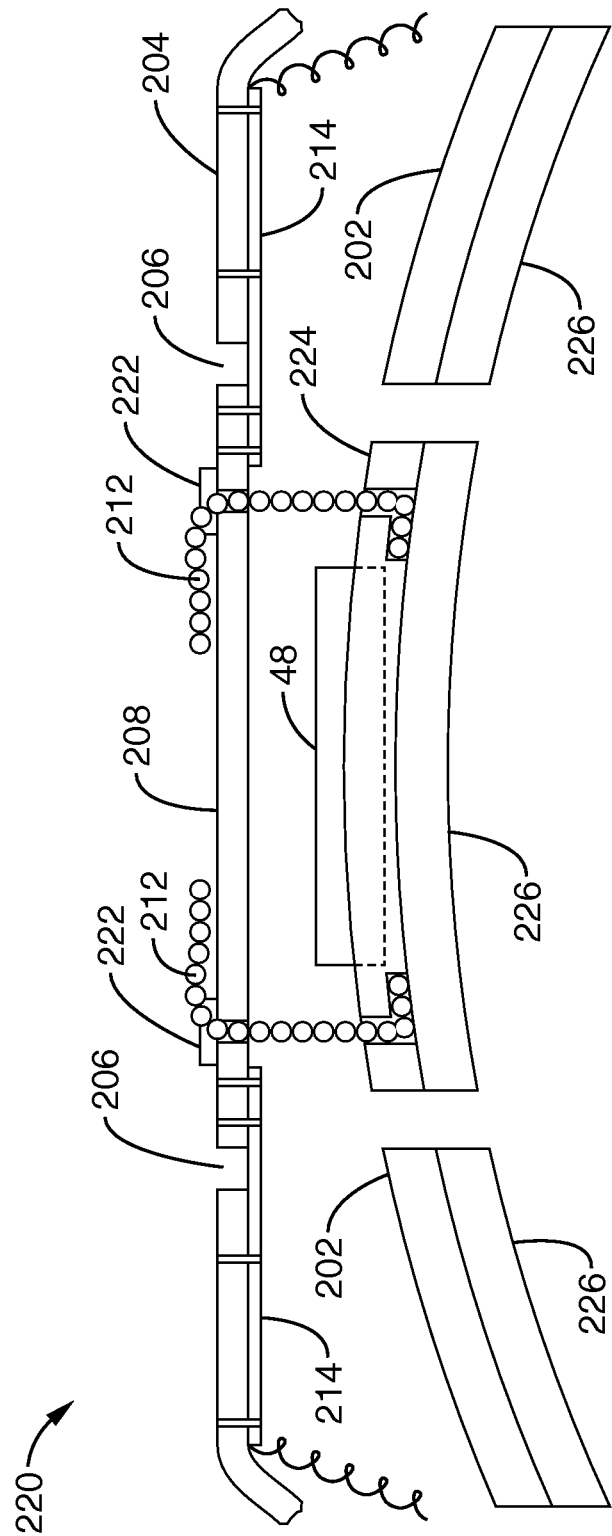

FIG. 17 is a side of another embodiment of the platform of the present invention.

Figure 18B:
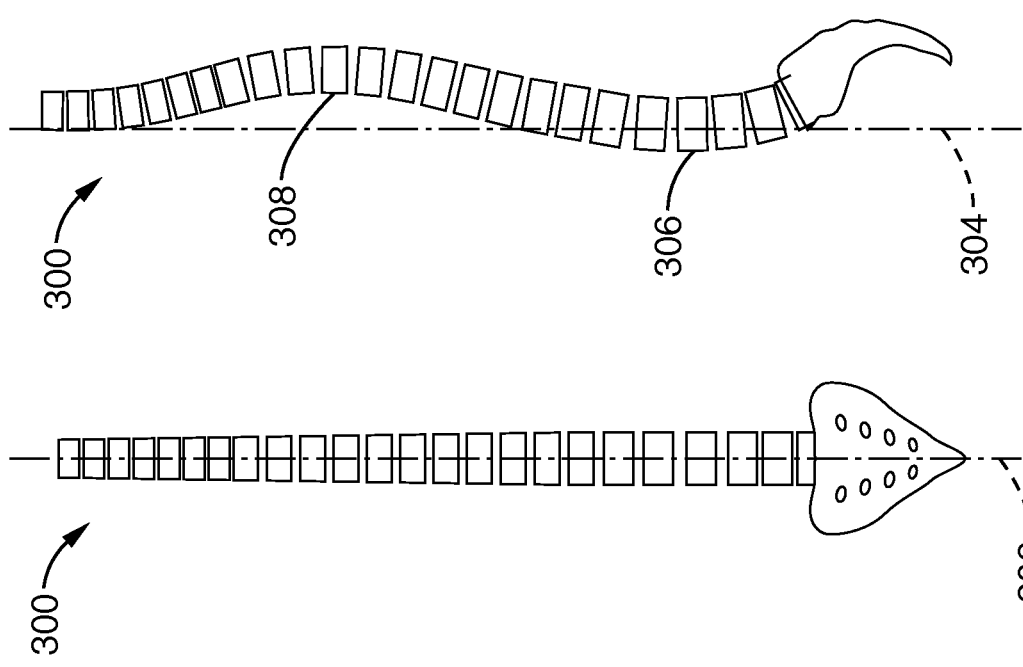
Figure 18A:
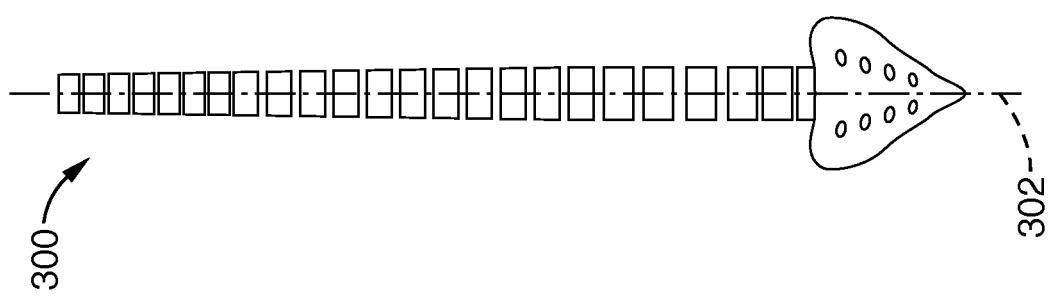

FIG. 18A is an anterior view of the human spine.

FIG. 18B is a lateral view of the human spine.

FIGS. 19A-D illustrate various abnormal curvatures of the spine due to scoliosis.

Figure 20:
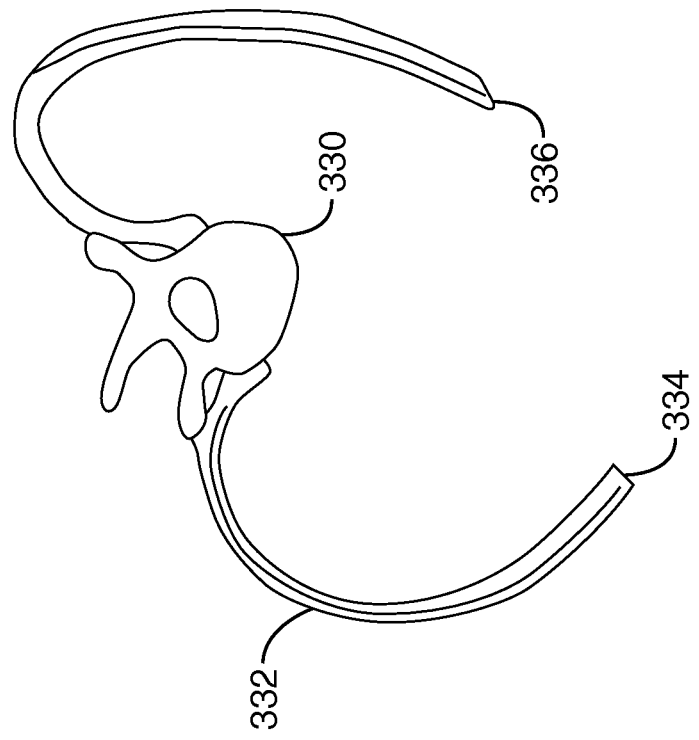

FIG. 20 illustrates abnormal rotation of the vertebrae of the spine as a result of scoliosis.

Figure 21:
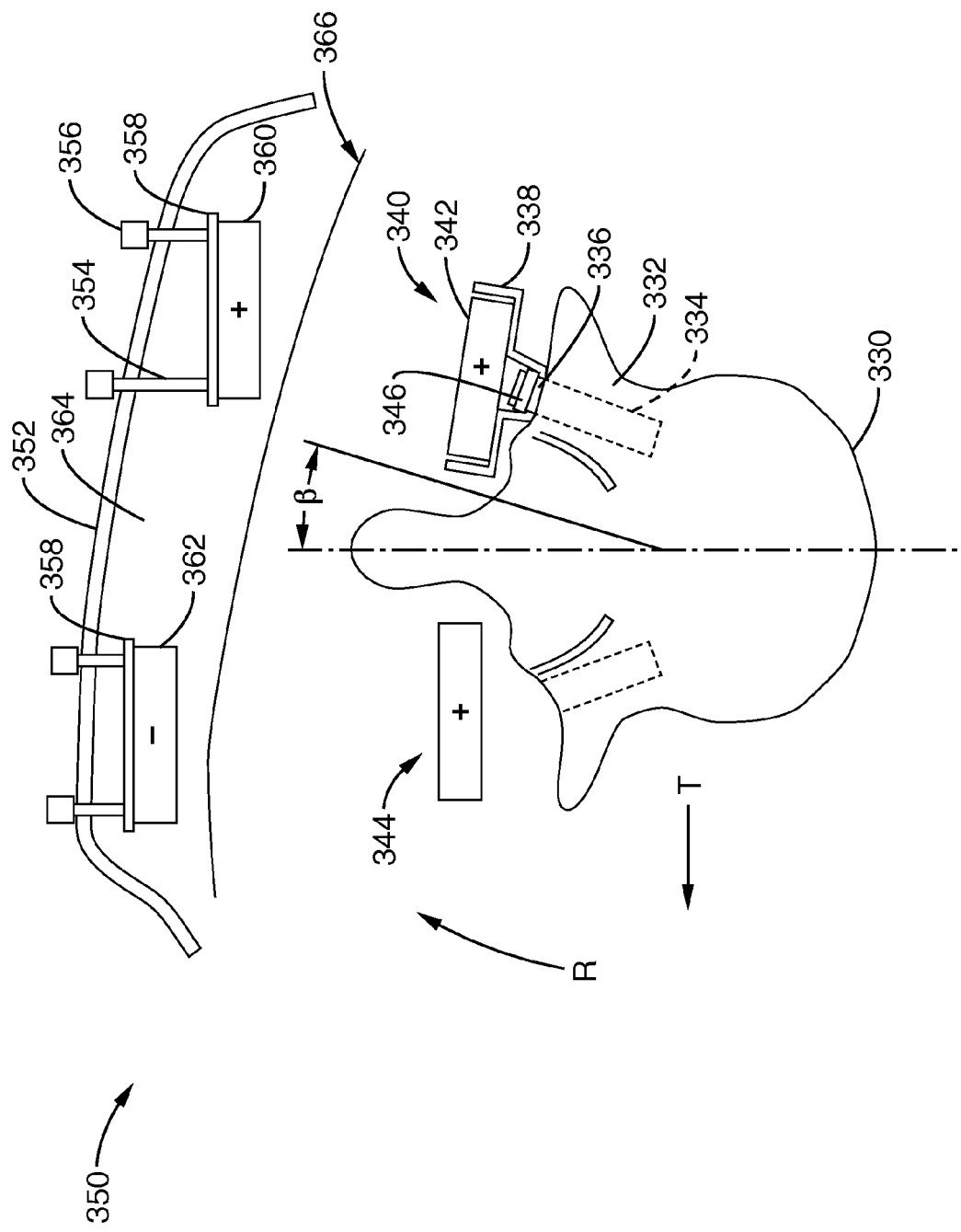

FIG. 21 illustrates another embodiment of the invention for treating scoliosis.

Figure 22:
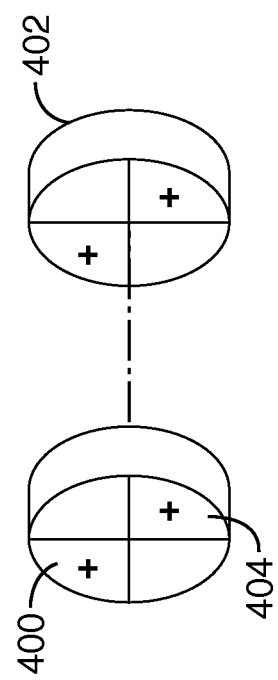

FIG. 22 illustrates an alternative embodiment for delivering a pulsed magnetic field to a body member.

Figure 23:
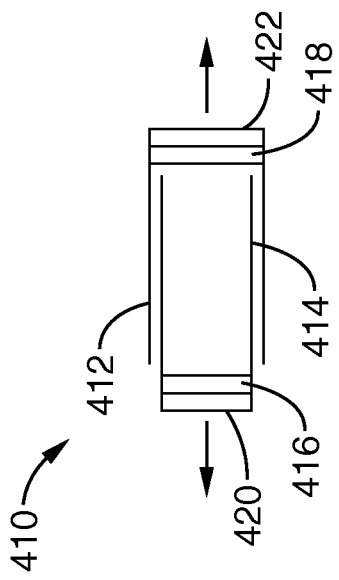

FIG. 23 is a schematic view of an alternative embodiment for delivering a repulsive force to a body member.

Figure 24:
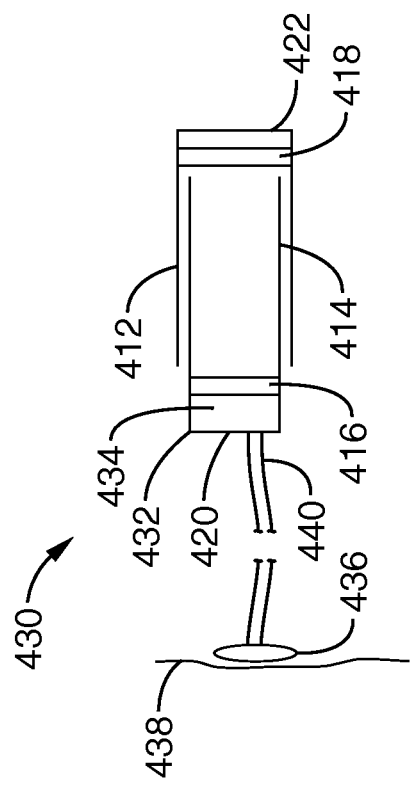

FIG. 24 is a schematic view of the device of FIG. 23 with a fluid pump.

Figure 25:
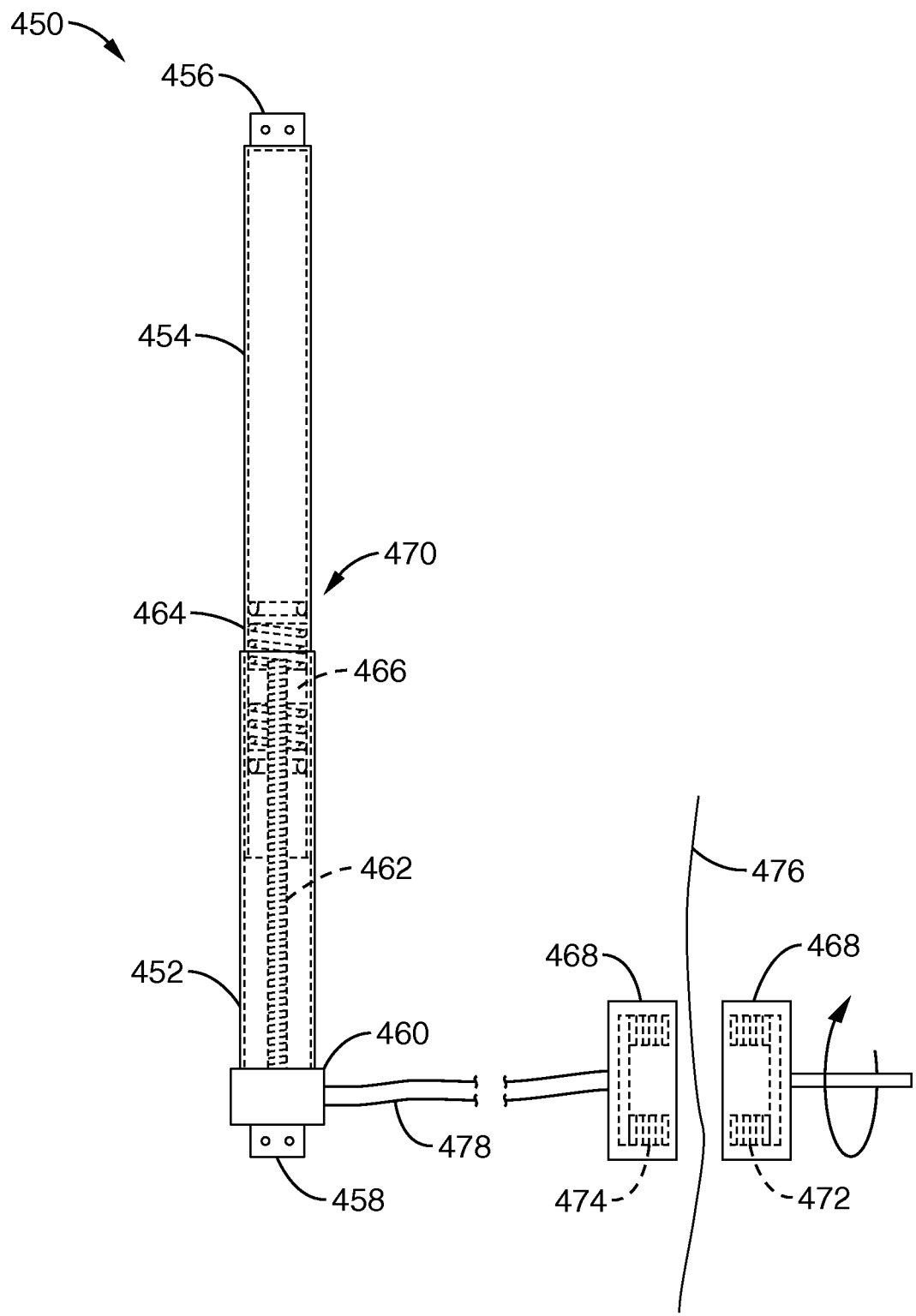

FIG. 25 illustrates an alternative embodiment of a repulsion device incorporating a mechanical jackscrew.

Figure 26:
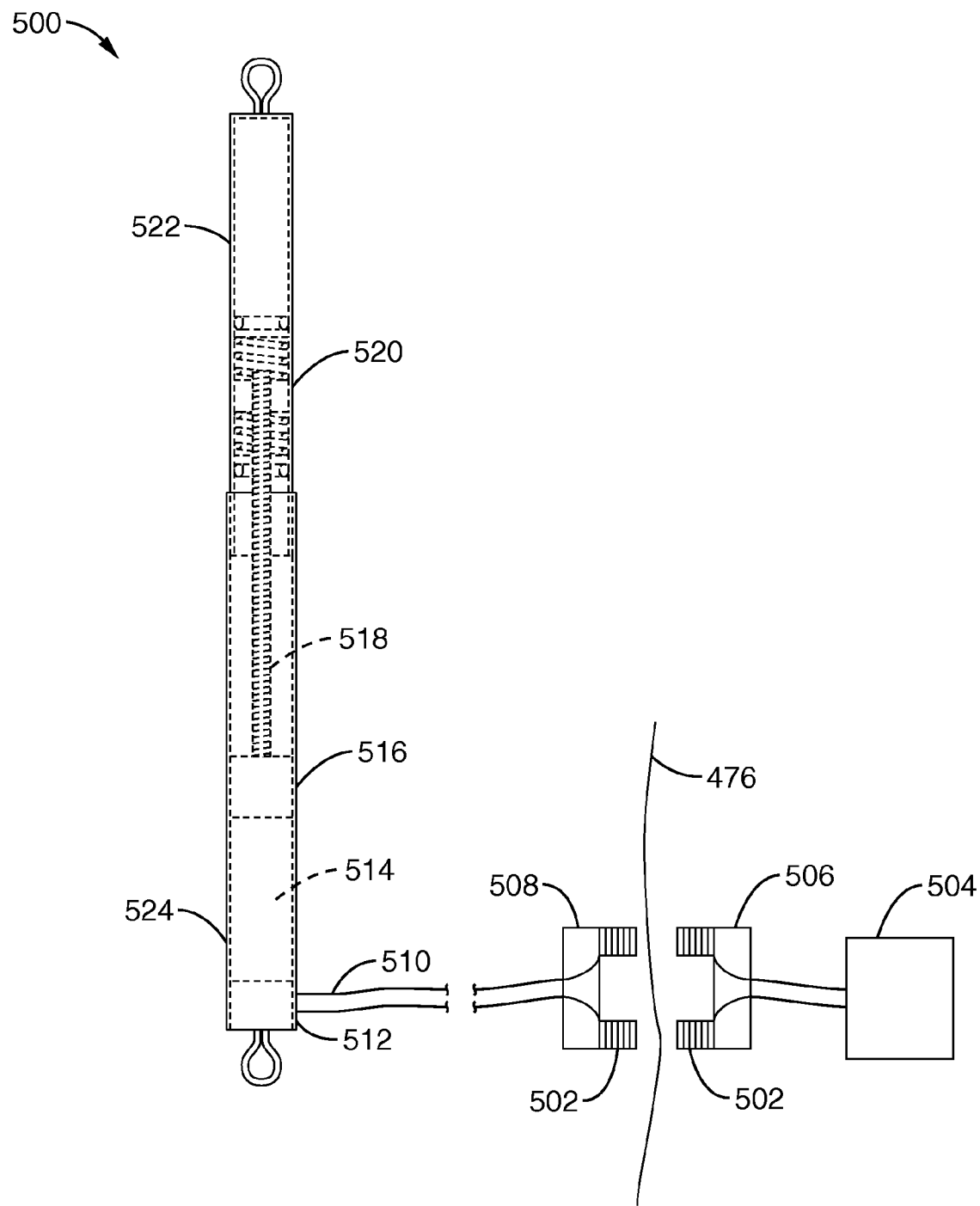

FIG. 26 illustrates an alternative embodiment of a repulsion device incorporating an electric jackscrew.

Figure 27:
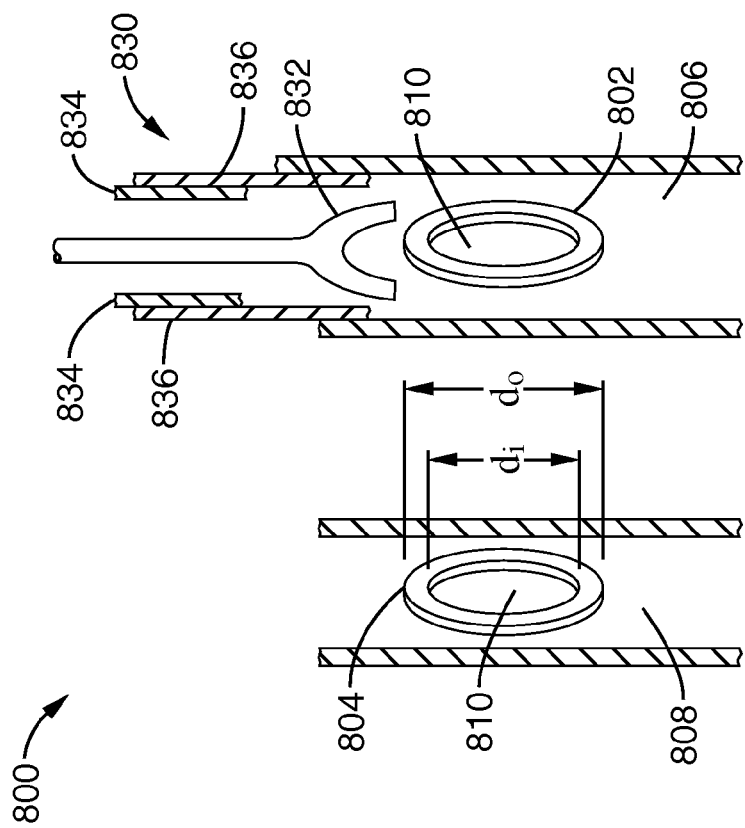

FIG. 27 is a schematic diagram for a system for performing auto-anastomosis between two internal organs using magnetic ring implants in accordance with the present invention.

Figure 28:
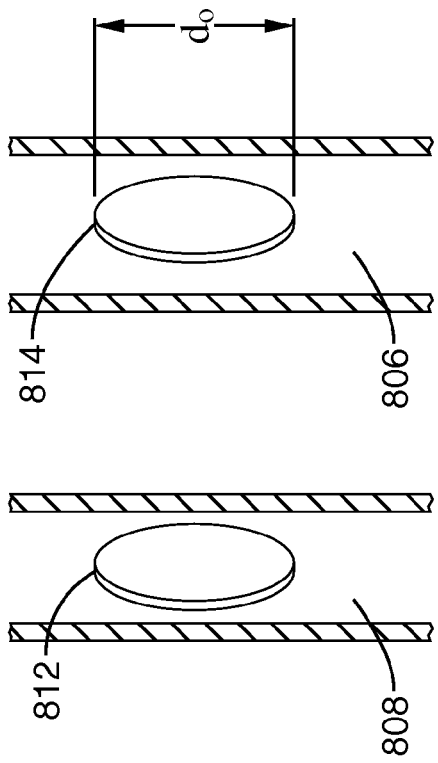

FIG. 28 is a schematic diagram for a system for performing auto-anastomosis between two internal organs using magnetic disc implants.

Figure 29:
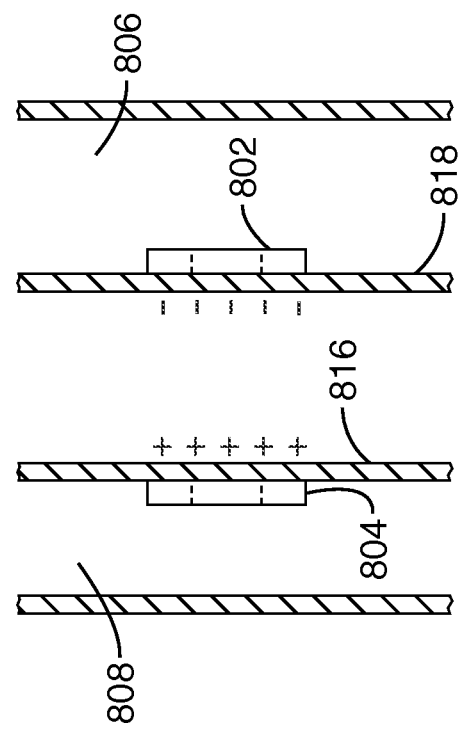

FIG. 29 is another view of the system of FIG. 27 showing the magnetic implants concentrically aligned.

Figure 30:
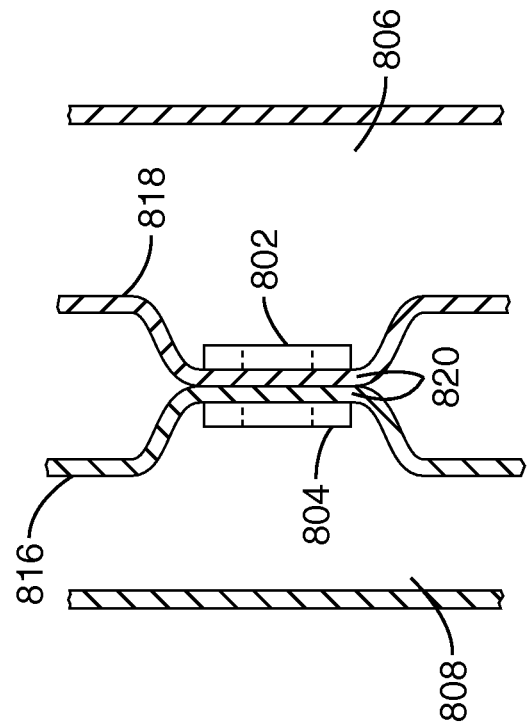

FIG. 30 shows the system of FIG. 27 with the magnets collapsing the visceral walls.

Figure 31:
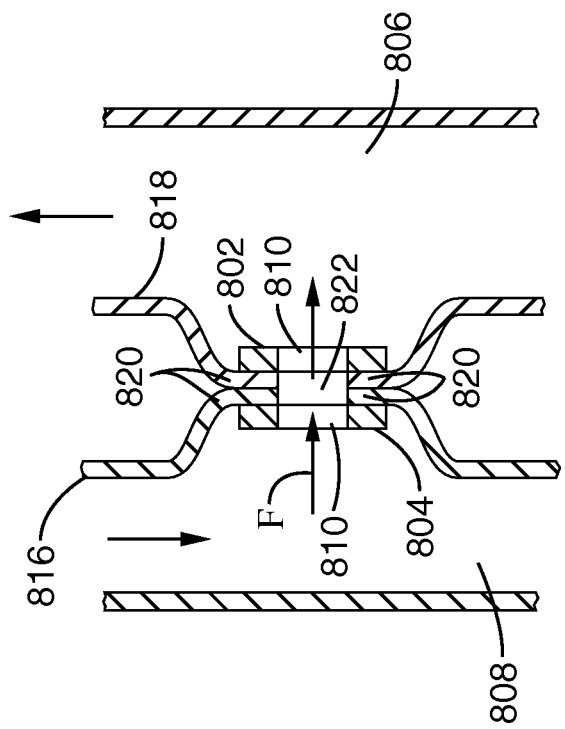

FIG. 31 is a view of the system shown in FIG. 27 with the tissue between the magnets cut out.

Figure 32:
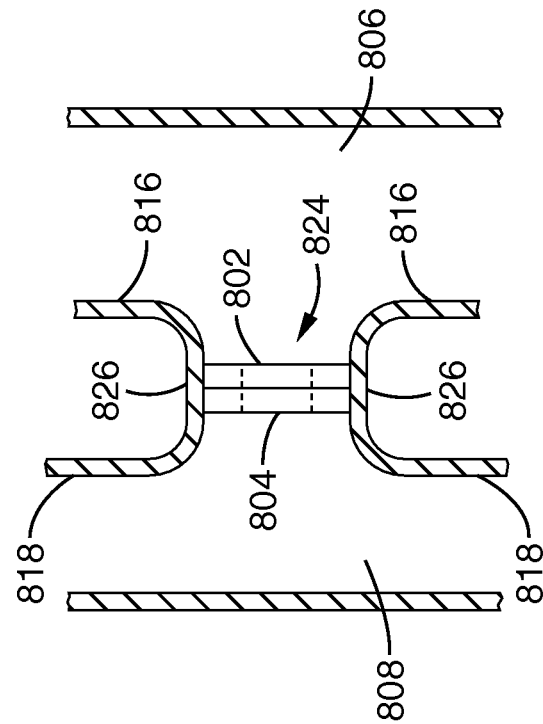

FIG. 32. illustrates the system of FIG. 27 after the tissue between the magnets has necrosed and fallen out, with accompanying anastomosis and fistula.

Figure 33:
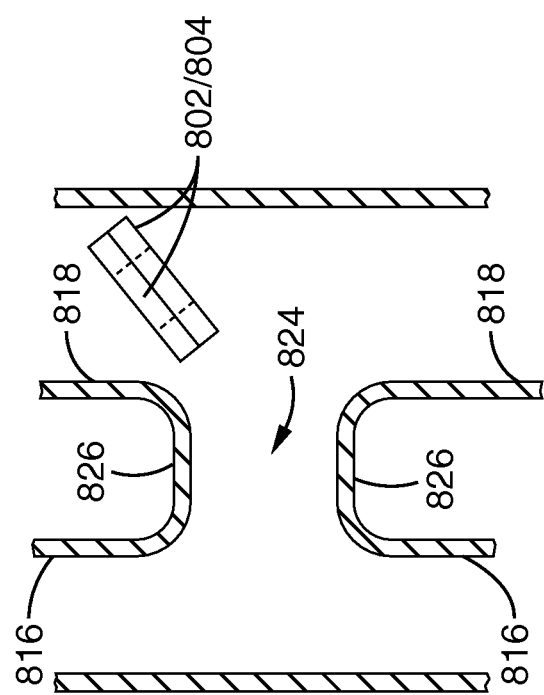

FIG. 33 illustrates the system of FIG. 27 after the magnets have fallen out of the fistula.

Figure 34:
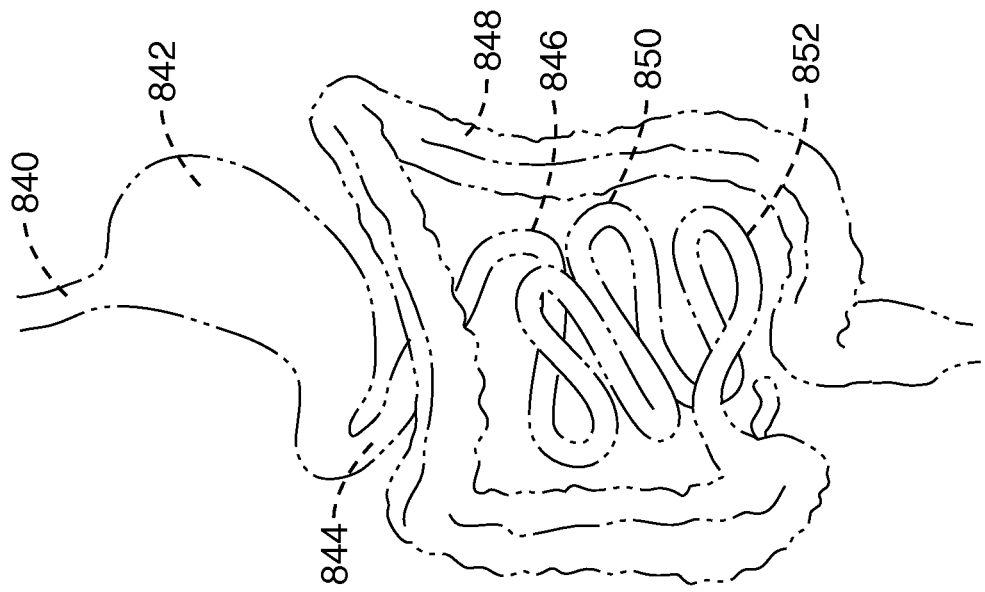

FIG. 34 illustrates an exemplary gastrointestinal tract.

Figure 35:
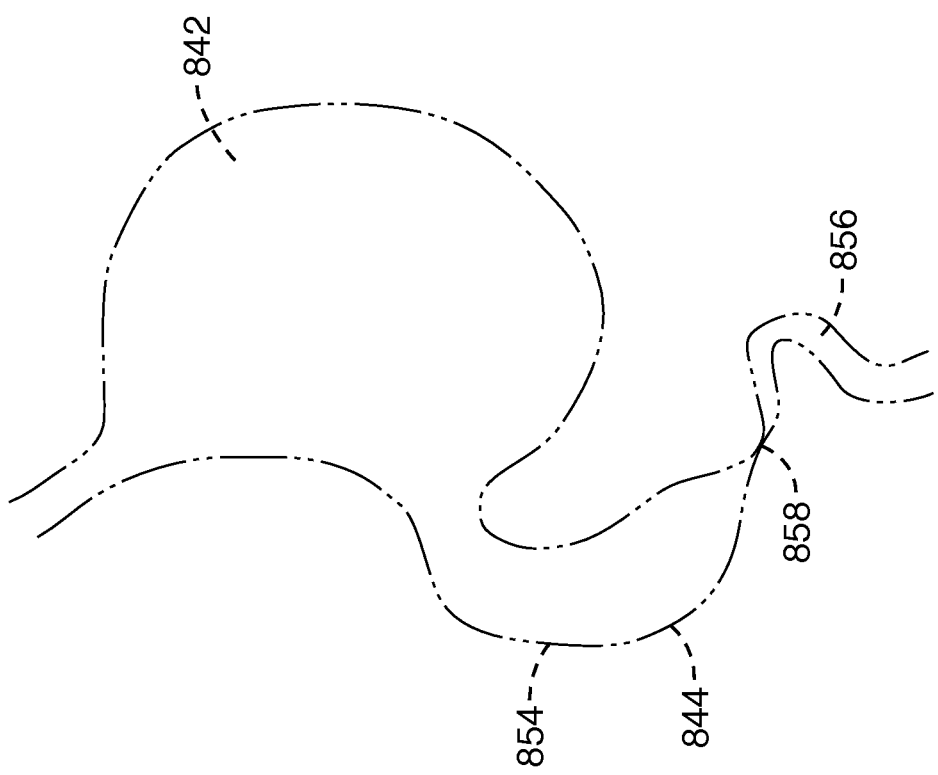

FIG. 35 illustrates a patient with duodenal atresia.

Figure 36:
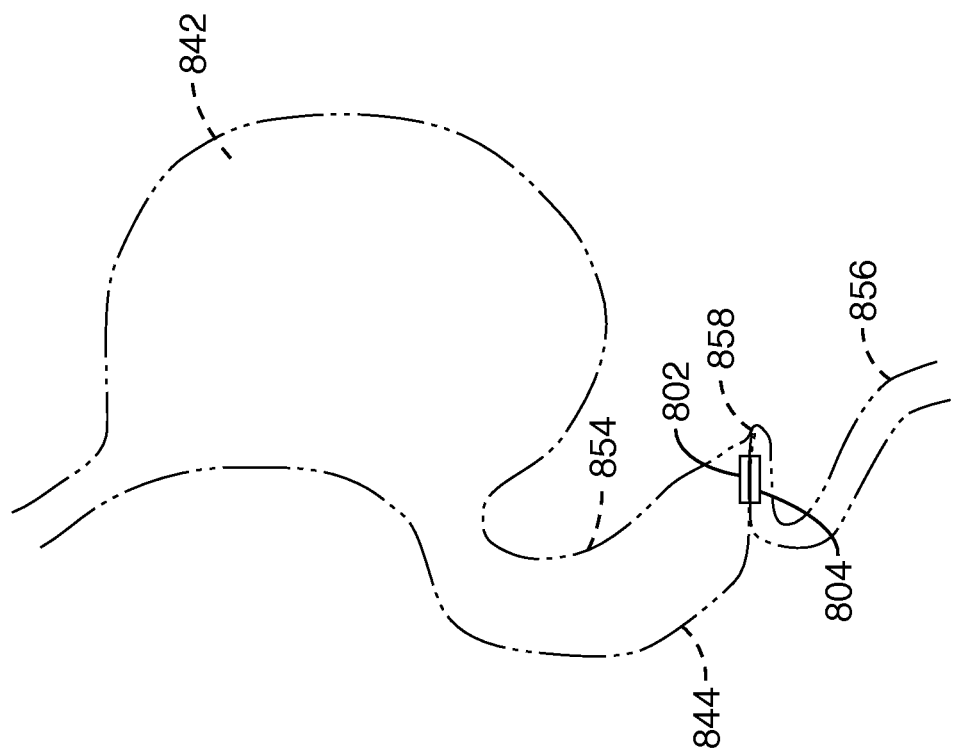

FIG. 36 illustrates a schematic diagram of the system of the present invention used to treat the duodenal atresial.

Figure 37:
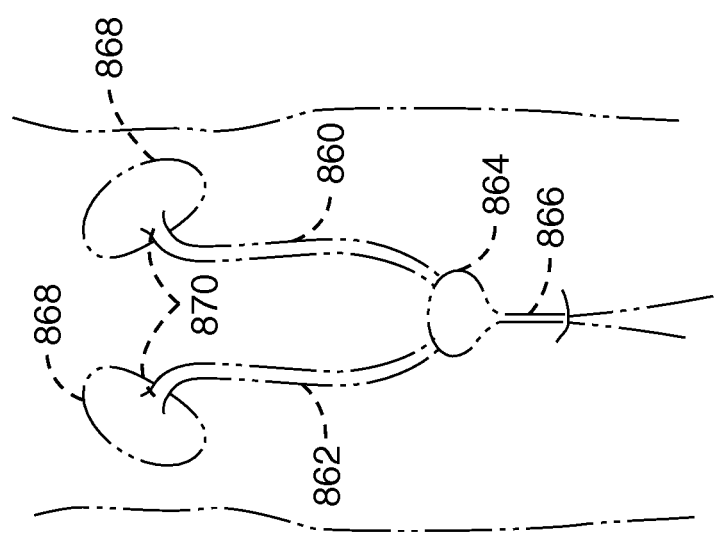

FIG. 37 illustrates an exemplary urinary tract.

Figure 38:
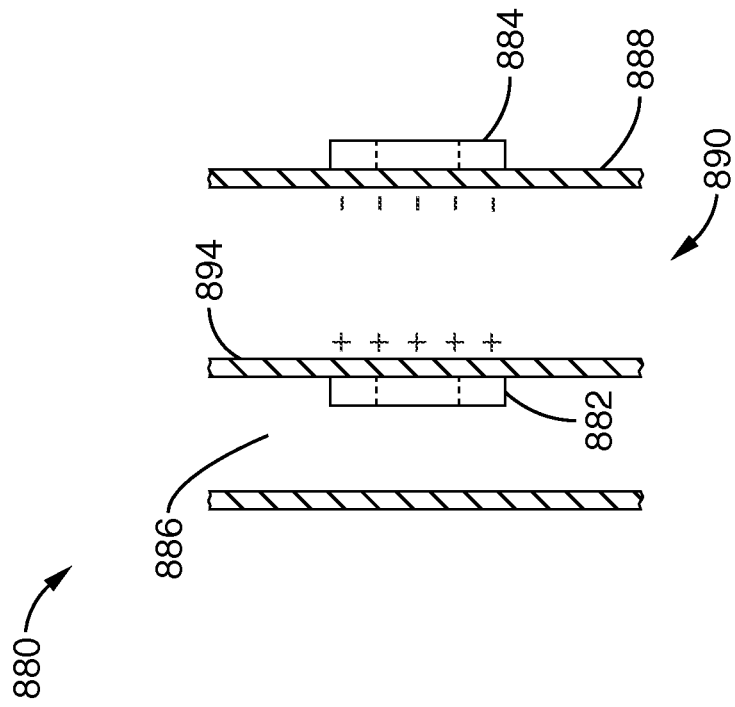

FIG. 38 shows a schematic diagram of a system for creating an ostomy using an internal magnet and external magnet in accordance with the present invention.

Figure 39:
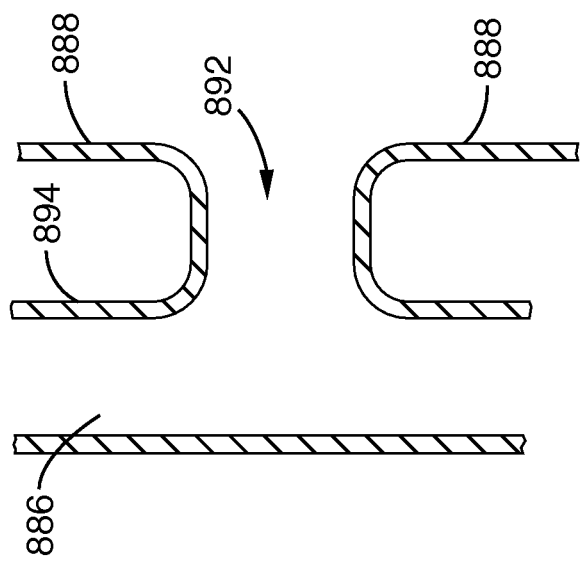

FIG. 39 illustrates a stoma in the abdominal wall created after implementation of the system of FIG. 38.

Figure 40:
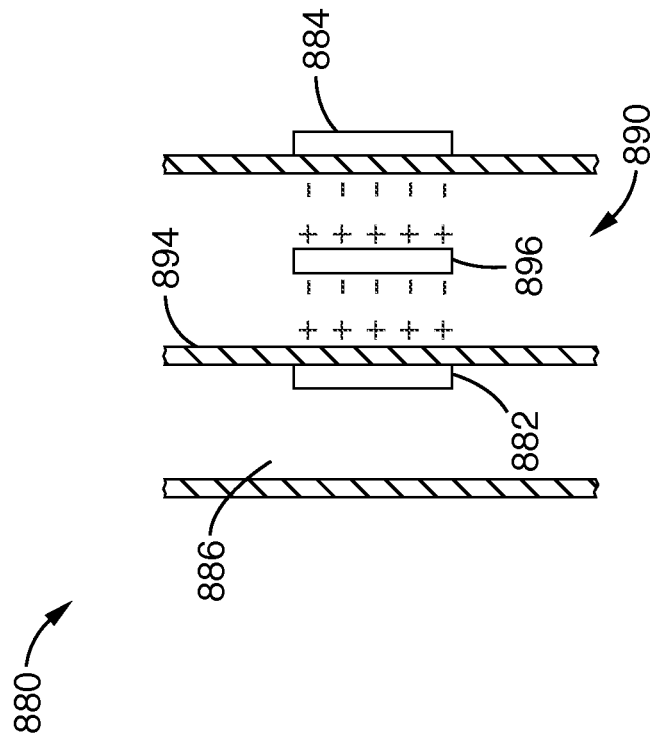

FIG. 40 illustrates the system of FIG. 38 using an intermediate internal magnet.

Figure 41:
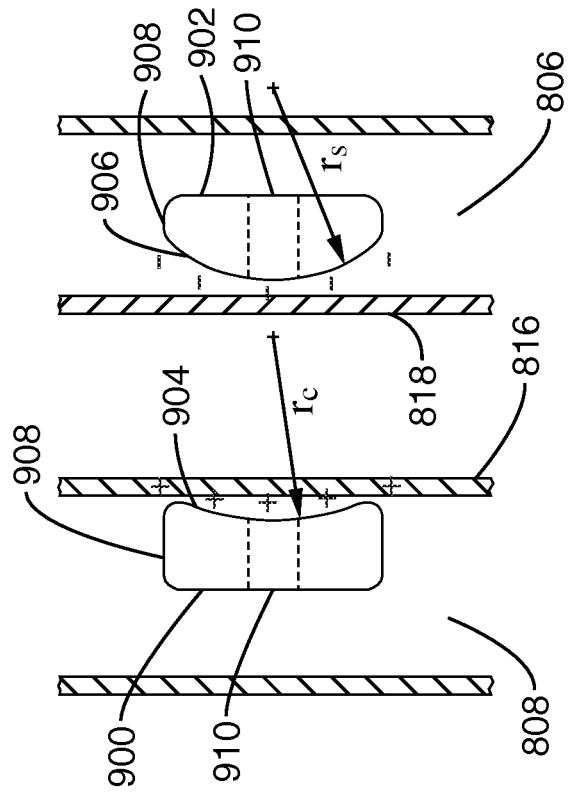

FIG. 41 illustrates two curvilinear magnets disposed opposite one another within two lumen segments inside a patient.

Figure 1:
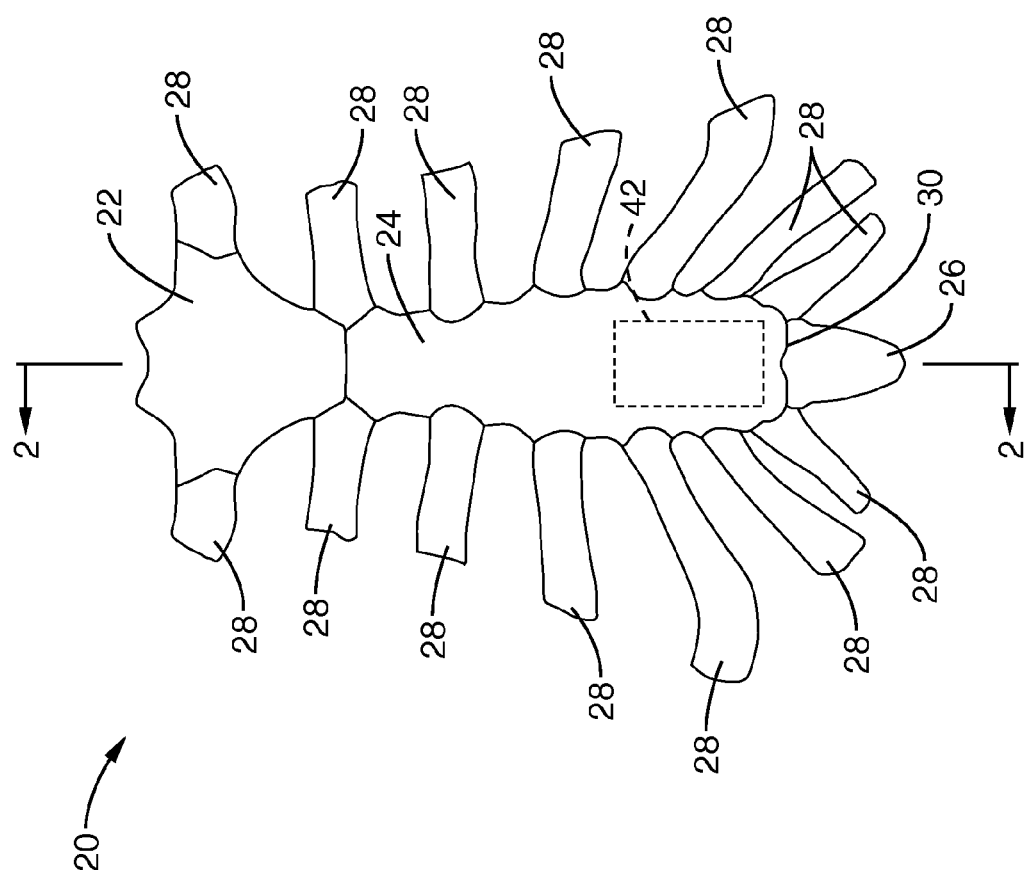
FIG. 1 is a schematic view of a human sternum with an implant according to the present invention installed under the sternum.
Figure 42:
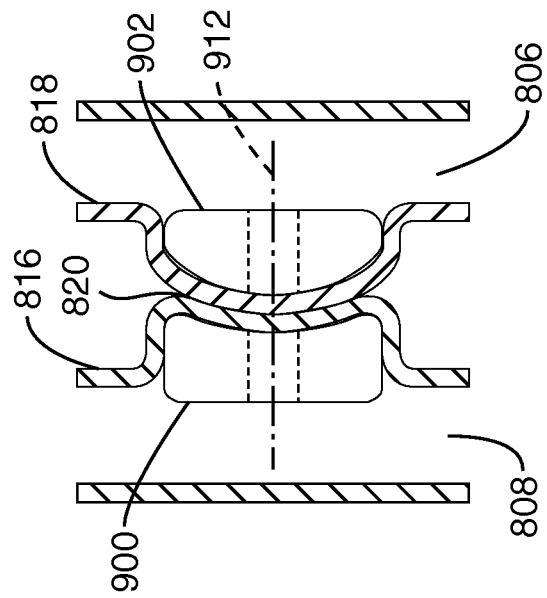

FIG. 42 shows the magnets of FIG. 1 compressing the walls of the two lumen segments.

Figure 43:
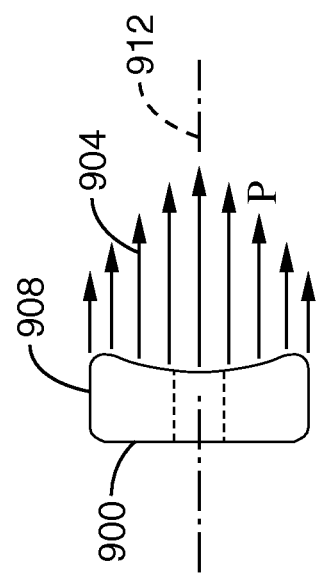

FIG. 43 illustrates a diagram of an exemplary non-uniform loading resulting from the curved surface of the magnet.

Figure 44:
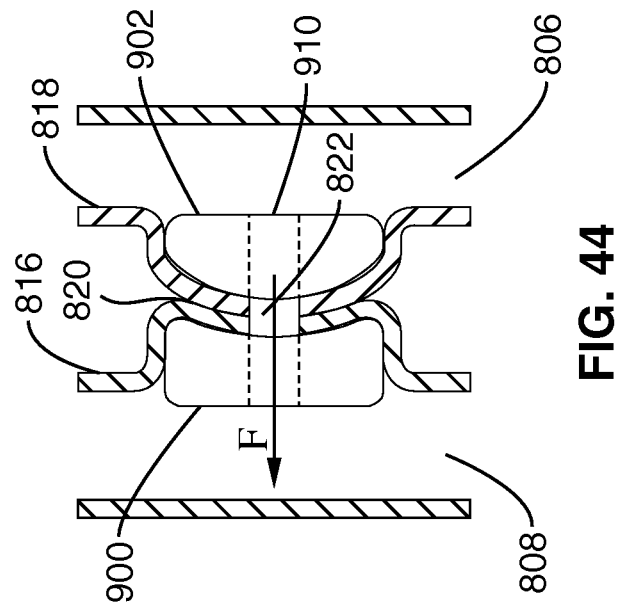

FIG. 44 shows a temporary aperture generated in the lumen tissue in accordance with the present invention.

Figure 45:
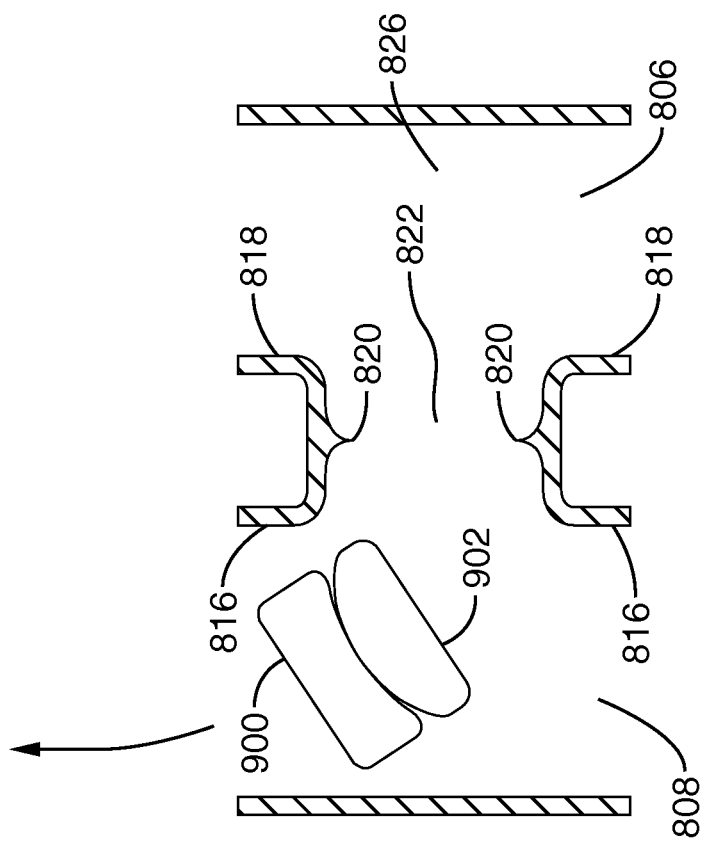

FIG. 45 illustrates a fistula created by the magnets of FIG. 1 in accordance with the present invention.

Figure 46:
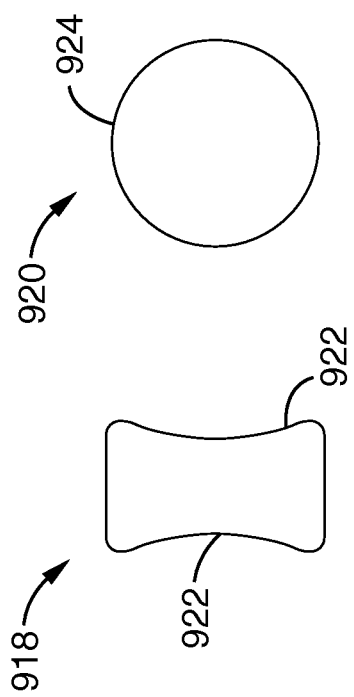

FIG. 46 illustrates an alternative embodiment of the magnets of FIG. 1 having additional curvilinear surfaces.

Figure 47:
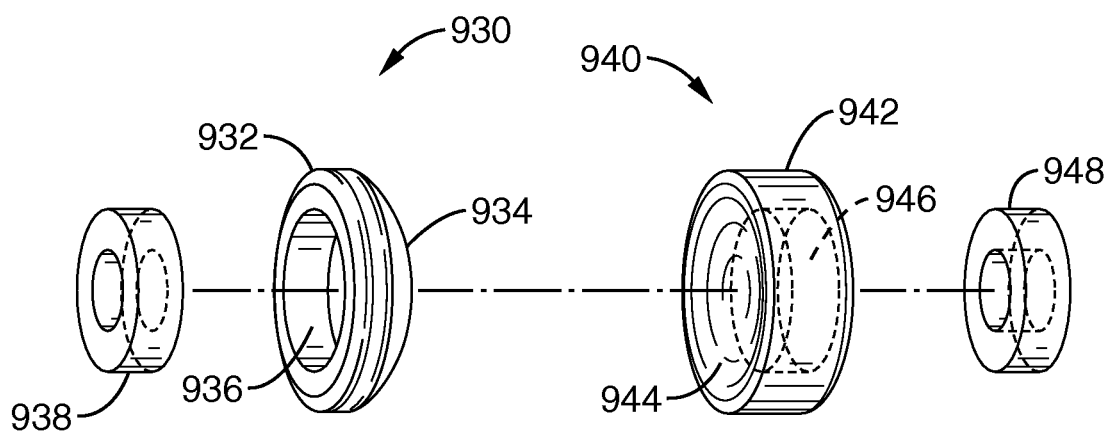

FIG. 47 is an expanded view of curvilinear magnet assemblies in accordance with the present invention.

Figure 48:
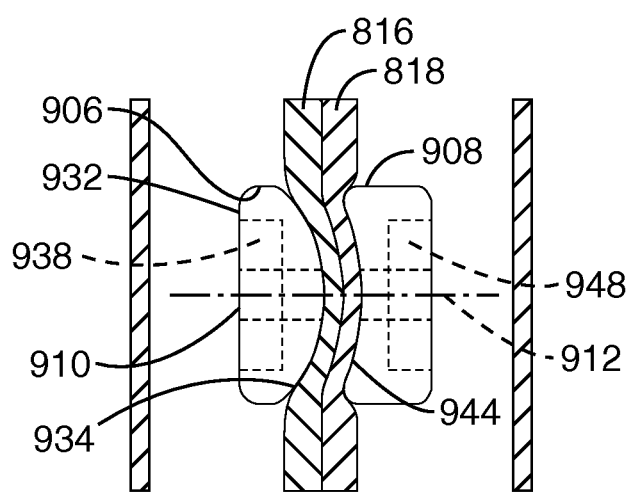

FIG. 48 is a schematic view of the curvilinear magnet assemblies of FIG. 47 positioned at a treatment site in a patient's body.

Figure 49:
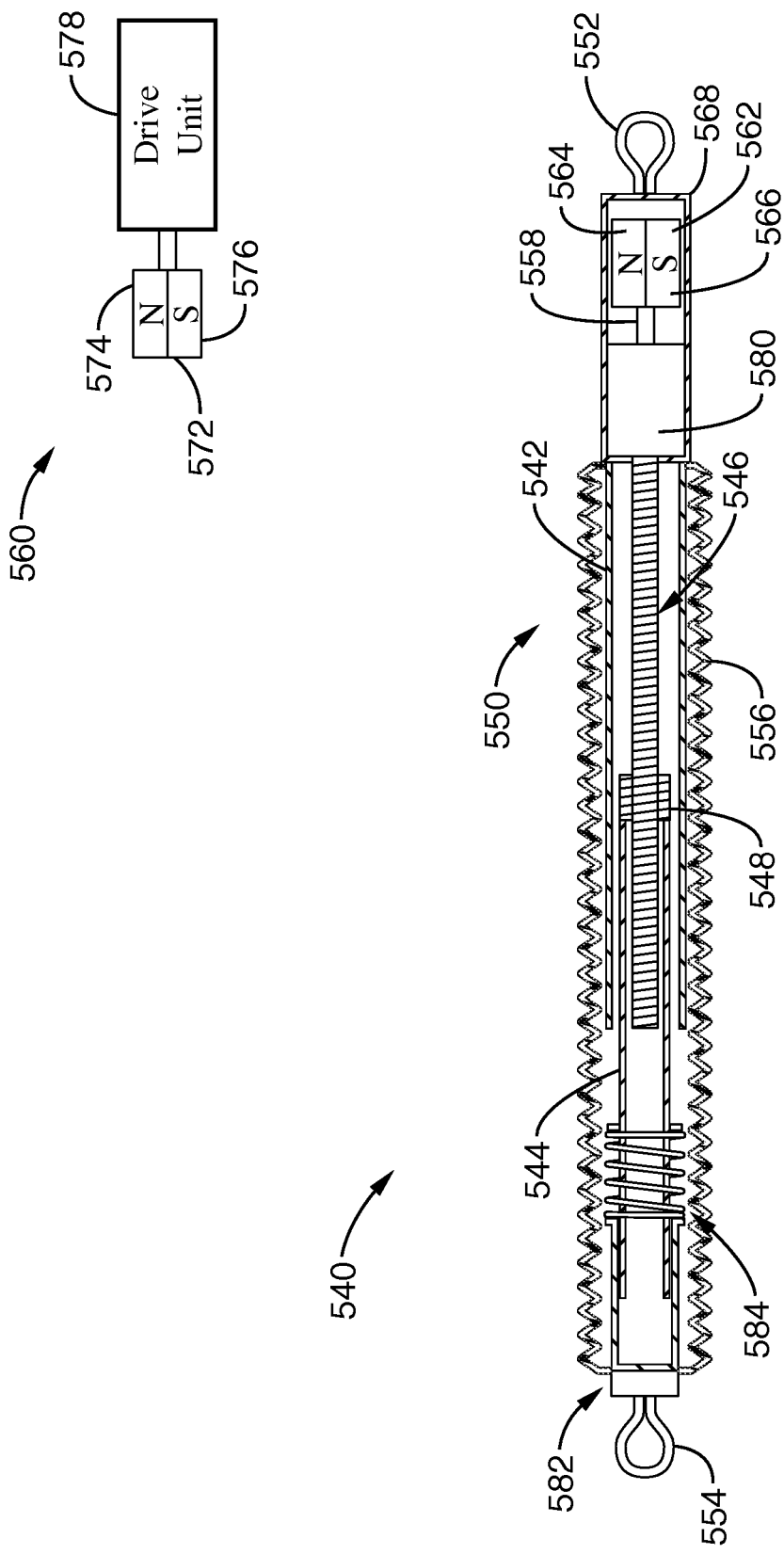

FIG. 49 is a view of an internal jackscrew assembly in accordance with the present invention.

FIG. 50 shows an expanded view of an internal magnet assembly.

FIG. 51 illustrates a cross-sectional view of the internal magnet of FIG. 50.

FIG. 52 illustrates the internal magnet assembly of FIG. 50 installed on the sternum of a patient.

Figure 53:
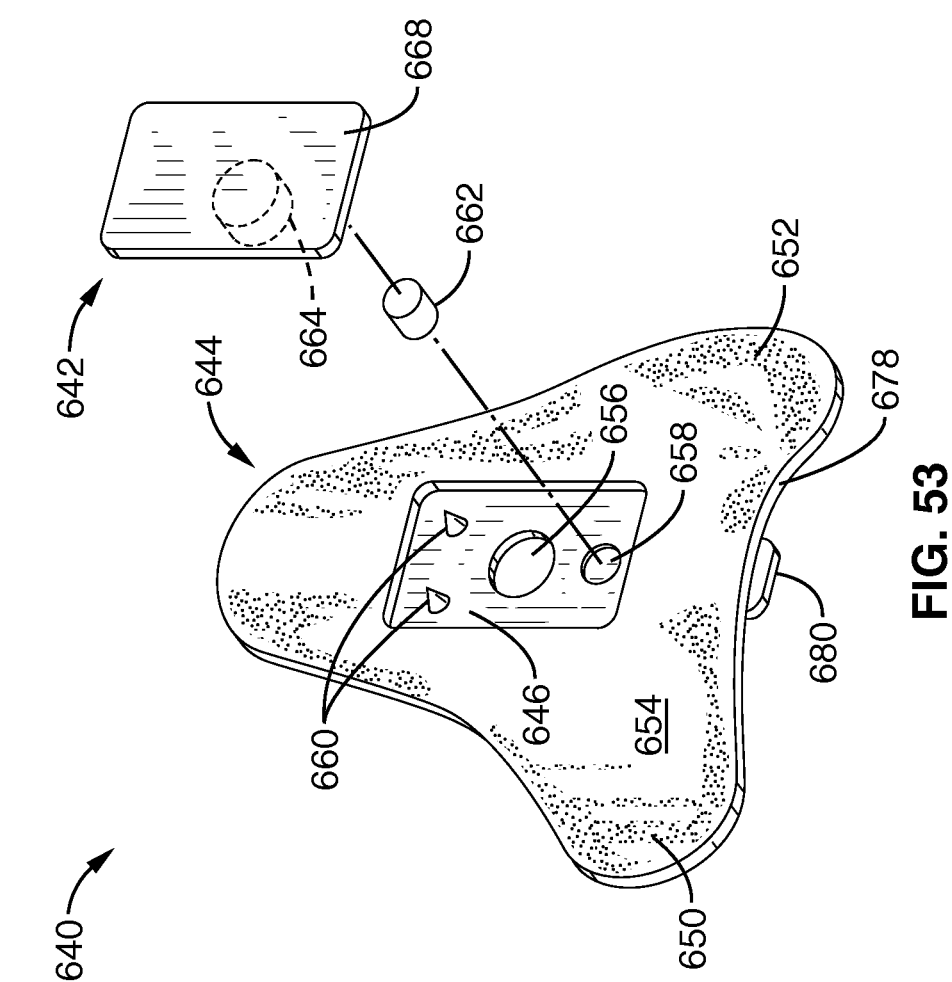

FIG. 53 is an expanded view of an external magnet mount in accordance with the present invention.

Figure 54:
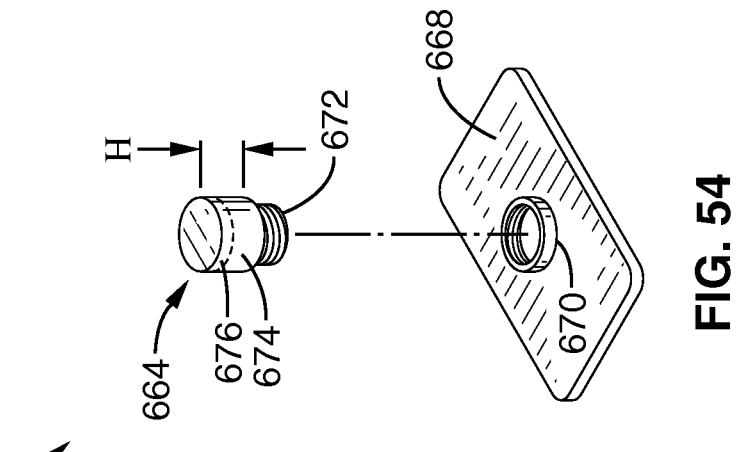

FIG. 54 is an expanded view of an external magnet configured to be used with the mount of FIG. 53.

DETAILED DESCRIPTION OF THE INVENTION

Referring more specifically to the drawings, for illustrative purposes the present invention is embodied in the apparatus and methods generally shown in FIG. 1 through FIG. 17 and FIGS. 21-26 and 27-40. It will be appreciated that the apparatus may vary as to configuration and as to details of the parts, and that the methods may vary as to the specific steps and sequence, without departing from the basic concepts as disclosed herein.

The present invention utilizes a system in which a small magnet is implanted in cooperation with an internal body member to apply a corrective force to the body member by virtue of its attraction to an adjustable magnet in an external device that is comfortable and cosmetically pleasing.

Small rare earth metal magnets can produce considerable force and can be manipulated in terms of size, shape and position. This force can be used to alter growth and development of skeletal structure and soft tissue. The biology of tissue response to force has been well studied. Clinical application of this powerful biologic principle has been limited by the difficulties of applying force through external bracing or through internal pins manipulated by external devices (e.g., bone lengthening through distraction osteogenesis). Magnetic force fields can be used to apply force to implanted magnets attached to an internal structure without violating the skin and soft tissue. The magnetic force field can be manipulated externally to adjust the direction, strength and speed at which the deformity is corrected.

1. Pectus Excavetum

FIGS. 1-16 illustrate a preferred embodiment of the invention relating to the correction of pectus excavetum. FIG. 1 illustrates a schematic, anterior view of a human sternum 20. The sternum 20 is an elongated, flatted bone, forming the middle portion of the anterior wall of the thorax. The sternum 20 generally consists of three parts: the manubrium 22, which at its upper end supports the clavicles (not shown); the body or gladiolis 24, which interfaces at its upper end with the lower end of the manubrium 22, and the xiphoid process 26, which interfaces at its upper end with the lower end of the gladiolis 24 at junction 30. The margins of sternum 20 articulate with the first of seven pairs of ribs 28.

Figure 2:
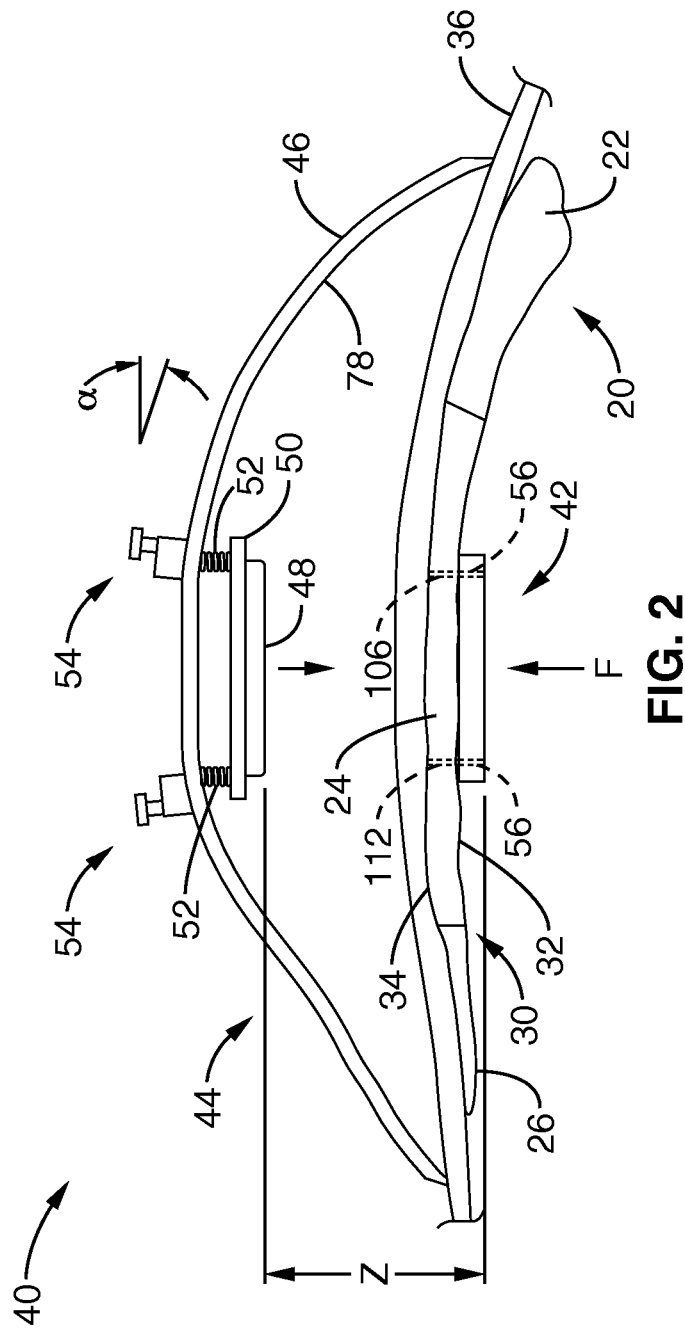
FIG. 2 is a cross-sectional schematic view of the platform of the present invention installed over a patient's chest and an implant installed under the sternum.

As shown in FIG. 1 and illustrated as a cross-sectional view of a corrected patient's chest in FIG. 2, a magnetic substernal implant 42 may be installed on the posterior surface 32 the body 24 of the sternum 20, just above the xiphoid process 26. Illustrated in greater detail in FIG. 3, the implant 42 preferably comprises a rare earth magnet 90, or an array of rare earth magnets housed in casing 92. The casing 92 may comprise any biocompatible material such as medical grade epoxy, titanium or suitable material used in the art. Casing 92 preferably has mounting holes 56 for fixation at each corner. The casing 92 may also have a plurality of protrusions 94 to enhance the attachment of the implant 42 with the sternum 20.

The magnetic implant 42 is sized to fit comfortably behind the sternum. An exemplary implant may 3 inches long, 2½ inches wide and ³⁄₁₆ thick. However, the size of the implant may vary according to patient anatomy.

FIG. 2 and FIGS. 5-13 illustrate an exemplary method of surgically installing the implant 42. A 3 cm substernal transverse incision 58 is made through the patient's skin 36. The ziphoid process 26 is then separated from the lower sternum body 24 and a pocket is bluntly dissected behind the posterior surface 32 of the sternum, as illustrated in FIG. 6.

The implant 42 is attached to the posterior surface of the sternum with sutury passed through the holes 112 in the sternum illustrated in FIG. 2. Using laparoscopic or arthroscopic visualization, a drill guide 100 is inserted and positioned over the proximal end of the sternum body 24, as shown in FIGS. 7 and 8. A small stab wound is made into skin 36, and the drill sleeve 102 is inserted through the guide 100. The sternum 20 is then drilled under direct visualization to bore one or more distal bores 106 from the anterior surface 34 of the sternum through to the posterior surface 32. Distal bores 106 preferably line up with the corresponding mounting holes 56 in casing 92.

Referring now to FIG. 9, a distal suture 108 is looped through one of the mount holes 56 of casing 92. The distal suture 108 preferably comprises a heavy braided suture commonly used in the art, e.g. #2 or #5 ticron. The suture is then fed under the sternum 20 and a suture retriever 110, such as a Hewson type, is used to pull the distal suture 108 through the corresponding distal bore 106 in the sternum body 24 and the anterior skin stab wound. The process is repeated for the second corner of the distal end of the casing 92.

Referring now to FIG. 10, the proximal end 114 of skin 36 and subcutaneous tissues from the anterior sternum proximal to the sterno-xiphoid junction 58 are pulled back to expose the proximal end of the sternum body 24. The drill guide 100 is moved transversely along the sternum body 24 to the exposed portion of the sternum under proximal end 114. Once sufficient exposure is obtained, one or more proximal bores 112 are drilled under direct vision through the sternum anteriorly-to-posteriorly, thus providing anchoring points for all corners of the casing 92.

Now referring to FIGS. 11 and 12, a proximal suture 116 is looped through one of the mount holes 56 on the proximal end of casing 92. The suture is then fed under the sternum 20 and suture retriever 110 is used to pull both ends of the proximal suture 116 through the corresponding proximal bore 112 in the sternum body 24. The process is repeated for the second corner of the proximal end of the casing 92.

As seen in FIG. 12, both sets of proximal and distal sutures 116, 108 are pulled to guide the implant 42 up behind the sternum 20 and maintain the apposition of the casing 92 to the sternum 20 with traction on the sutures.

Referring now to FIG. 13, the proximal sutures 116 are tied down firmly over the sternal bone bridge to secure the implant 20 to the proximal surface 32 of the sternum. Under direct vision, the process is repeated for the distal sutures 108.

Although FIGS. 9-13 illustrate a preferred embodiment using suture to fasten the implant 42 to the sternum 20, it is appreciated that any number of different fastening means commonly known in the art may be used to secure the implant 42. For example, bolts (not shown) may be passed through bores 106, 112, threaded into threaded mounting holes 56 of casing 92 and torqued down to secure the implant 42 to the posterior surface 32 of the sternum 20. Alternatively, the implant may be fastened to either the posterior or anterior sides of the sternum via cables that wrap around the sternum. In this configuration, since the implant is closer to the platform, the internal magnetic member may be any magnetically responsive material, such as an iron plate with biocompatible coating (e.g. titanium).

Surgical placement generally requires a brief outpatient general anesthesia. The procedure takes about 30 minutes and requires minimal post-operative analgesia.

FIGS. 2 and 14-17 illustrate several embodiments of an external magnet platform of the present invention for treating pectus excavatum. FIGS. 14 and 15 show an embodiment having a platform 40 configured to be worn over a patient's chest. Platform 40 comprises a chest plate 44 sized according to the patient's anatomy. Generally, a mold is made of the individual's chest deformity. From this the desired end point position of the sternum and chest wall shape are molded to create the chest plate 44. FIG. 14 is a bottom view of platform 40, showing the underside 78 of chest plate 44. In addition to being contoured to comfortably rest on the patient's chest, the underside 78 of the chest plate is cut away to create cavity 68 that allows the chest to expand outward as a result of treatment.

In a first configuration, an external magnet 48 is hung from the underside 78 of the chest plate 44 by a plurality of adjustment cables 62. External magnet 48 is preferably a rare earth magnet, or array of rare earth magnets. The external magnet has an adjustable stage, or mounting plate 50, which has a plurality of holes 70 to secure cables 62. As illustrated in FIGS. 14 and 15, the magnet 48 is hung with 4 cables. However, other configurations, such as a three cable design (not shown), may also be used. The cables 62 are coupled to the chest plate via adjustment members 54. Cables 62 lead from the magnet plate 50 out to the exterior surface 46 and back through to the underside of the chest plate via through holes 64 to terminate at adjustment member 54. One or more biasing springs 52 may be imposed between the chest plate 44 and the magnet 48, creating a tensile force on cables 62 so that the magnet is biased to the furthest orientation away from the chest plate 44 that is allowed from the cables' length.

By turning adjustment member 54 from the top of the chest plate illustrated in FIG. 15, the cable 62 may be shortened, thereby advancing one corner of the magnet plate 50 upward toward the chest plate 44. By rotating the adjustment member in the opposite direction, the cable is extended, thereby advancing one corner of the magnet plate 50 toward from the patient's chest and away from the chest plate 44. When all the adjustment members are moved the same increment, the magnet will translate toward or away from the patient's chest in the Z axis (see FIGS. 2 and 14). The magnet may also be rotated angle θ about the X or Y axis by manipulating the adjustment members 54 to lengthen or shorten one or more cables 62 with respect to the remaining cables.

The external magnet 48 and the implant magnet 90 are configured so that their opposite poles face each other, thereby generating an attractive force between the two magnets. By manipulating the distance of the external magnet 48 from the chest plate 44 in the Z direction, the amount of force applied to the internal magnet can be incrementally tuned or adjusted. By manipulating the orientation of the external magnet 48 with respect to the chest plate 44 in the X and Y directions, the direction of force applied to the internal magnet can be incrementally adjusted.

The chest plate 44 is preferably comprised of a rigid material, such as a rigid thermoplastic or polymer or steel reinforced polymer that does not deform as a result of the magnetic forces, allowing external magnet 48 to remain stationary with respect to the patient's chest. As a result of the constant force applied from the external magnet 48, the implant 42 imposes a corrective outward force F on the posterior surface 32 of the sternum 20. This outward force incrementally repositions/deforms the sternum 20 to move outward from the patient's chest cavity. By adjusting the angle of the external magnet in the X and Y directions, the force generated on the implant 42 may be directed to orient the sternum in the X and Y axes as well to correct asymmetric lesions.

An initial adjustment of the platform is made after the implant is placed in the outpatient surgical procedure. When the sternum 20 and implant 42 move toward the external magnet 48, the force generated between the magnets increases. If this force becomes too great and becomes uncomfortable for the patient, the magnet may be retracted toward the chest plate 44, thereby returning the magnetic force to the optimum comfort level for the patient. This process may be repeated for a number of intermediary steps, until the sternum 20 is gradually repositioned and/or deformed toward the desired final position and orientation.

The platform 40 may also include a strain gauge 74, or other force measuring means, to accurately determine the force being generated by the magnets. Strain gauge 74 may be connected via lead wires 76 to various points on the magnet plate 50 so that the pressure on each quadrant of the magnet may be accurately assessed. Strain gauge 74 may also comprise an LCD display (not shown) so that the patient or physician may readily assess whether the external magnet 48 is properly oriented, and adjust the magnet if need be.

The platform 40 is held in place by the magnetic pull between the two magnets, and in addition may be secured in place with a loose elastic band (not shown) around the chest. The principal force holding the platform 40 in place is the magnetic field itself. The patient may adjust the platform 40 to comfort and thus ensure against pressure damage to soft tissue. The patient may be taught to how to manipulate the external magnet 48 up and down to adjust and balance the force pulling the sternum 20 outward.

To provide extra comfort to the patient, and prevent the any unwanted manipulation of the adjustment members, a cover, such as that shown in FIG. 16, may be provided to cover the chest plate while the platform is being worn.

A preferred embodiment of the invention incorporating a bridged platform 200 is illustrated in FIGS. 16 and 17. Platform 200 has a chest plate 202 having a support 204 with opening 206 at it center. Chest plate 202 and support 204 may be separate pieces fastened together as shown in FIG. 16, or one integrated piece (not shown). Load member 208 is positioned in the opening 206 of support 204, and is bridged by a plurality of thin beam force sensors 214.

Load member 208 has a plurality of adjustment members 210 that retain magnet plate 50 and magnet 48 via a hanging means 212. Adjustment member 210 comprises an in-line screw, such as a jack-screw, lead screw, ball screw, or the like, which is hollowed out to support hanging means 212. As shown in FIGS. 16 and 17, hanging means 212 comprises a ball chain, but may also comprise a cable, wire, or the like. Alternatively, adjustment members 210 may comprise extended screws (not shown) that terminate a ball joint in magnet plate 50.

Adjustment members 210 may be manipulated to lower or raise the magnet 48, or adjust the angle of the magnet, as described in the embodiment of FIGS. 14 and 15. By turning screw 210 clockwise, one quadrant of the external magnet 48 may be precisely lowered to change the angle of the external magnet 48 with respect to the patient's chest, thereby changing the direction of the force applied to the implant 42. By turning all the screws the same clockwise increment, the magnet is lowered to generate a larger attractive force on the implant. Correspondingly, counter-clockwise rotation raises the external magnet to lower the attractive force on the implant 42.

When the platform is placed against the patient's chest, the attractive force between the implant 42 and the external magnet generates a load on load member 208. This load is sensed at all four quadrants by the thin beam force sensors 214. Readings from the sensors 214 are received by a force measuring means, such as the strain gauge 74 illustrated in FIG. 15, to provide accurate data on the force applied at each quadrant of the external magnet. This enables the treating physician or patient to accurately assess corrective the force being applied to the sternum, and modify the force if not at the desired level.

FIG. 17 illustrates an alternative embodiment having a platform 220 wherein the adjustment member comprises a clasp 222 for incrementally adjusting the extended length of ball chain 212, which is attached to each corner of the external magnet cradle 224. By changing the position at which the clasp 222 engages the ball chain 212 (similar to adjusting a necklace of bracelet), the height at any one quadrant of the magnet 48 may be changed with respect to the patient's chest to vary the force or direction of the corrective magnetic field. Chest plate 202 and cradle 204 may also have a layer of padding 226 to provide further comfort for the patient.

Over time, the steady gradual force applied to the sternum stretches the ligaments connecting the sternum 20 to the ribs. The sternum 20 itself may also deform as a result of the magnetic forces. The result is a reoriented and/or repositioned sternum without the characteristic depression of the pectus excavatum deformity.

As the sternum 20 moves closer to the external magnet 48, the patient or physician will typically readjust the position of external magnet 48 farther up into the chest plate. This is easily accomplished by adjusting the length of the four ball chains that suspend the magnet cradle 224.

FIGS. 50-52 illustrates another preferred embodiment of internal magnet assembly 600 configured to be mounted such that the internal magnetic implant is located on the anterior surface of the sternum 20. As shown in FIGS. 50 and 51, a sealed magnet assembly 602 comprises a hermetically sealed casing 608 that holds a magnet 604 and magnet retention cup 606 inside housing cover 610. The housing cover 608 may be laser welded to the housing 608 for proper seal. The housing cover 608 also is configured to receive a threaded post 612 that is sized to pass through a hole 628 drilled in the sternum 20, as illustrated in FIG. 52.

Referring to FIG. 52, a lower fixation assembly 620 is configured to be positioned at the posterior surface 32 of sternum 20. The lower fixation assembly 620 has a plate 622 and female threaded post that is configured to receive male threaded post 612 from the sealed magnet assembly 602. Plate 622 comprises a plurality of fixation points 624 that fixedly engage the bone of posterior surface 32 of the sternum 20. When the threaded post 612 of the sealed magnet assembly 602 is threaded into the receiving post 626 of the plate assembly 620, a compressive force is generated between the lower surface of the magnet housing 608 and plate 622, driving fixation points 624 into the bone mass of the sternum. Thus, in this configuration, the internal magnet assembly 600 is rigidly attached to the sternum 600 so that it may evenly distribute the load generated from the attractive force generated between it and the externally mounted magnet.

A washer-shaped spacer 614 may optionally be used to be positioned between the magnet housing 608 and upper sternum surface 34. Spacer 614 has a through hole for post 612, and may be sized accordingly to affect a desired height of the magnet above the sternum 20. The spacer 614 may also be formed of a semi-compliant material that conforms to the non-planar and irregular upper surface 34 of the sternum 20.

One or more suture hoops 630 may also be fixed (e.g. laser welded or otherwise fastened) to the magnet housing cover 608.

FIG. 53 illustrates another preferred embodiment of an external magnet platform assembly 640 for treating pectus excavatum or like deformities. The assembly 640 comprises a platform or chest plate 644 configured to be worn over a patient's chest and sized according to the patient's anatomy. The chest plate 644 may be made from a plastic-injection mold corresponding to the individual's chest deformity. The chest plate 644 is generally triangular shaped, with an upper arm 648 positioned upward, and two lateral arms 650 and 652 that arch around a portion of the patient's chest.

The chest plate 644 upper surface 654 has a recess 646 configured to receive external magnet assembly 664, with a through hole 656 so that external magnet housing 664 may be hung from the chest plate 644 and over the patient's chest. The underside 678 of the chest plate 644 is arched to create a cavity that allows the chest to expand outward as a result of treatment. The recess 646 is has a depression 658 configured to house a sensor 662. The sensor sits in the depression 658 so that a portion of the sensor rests above the housing floor, and forms a three-point contact along with protrusions 660 when the external magnet assembly 642 is placed in the recess 646. Thus, any downward force generated on the magnet assembly 642 is registered on the sensor 662, and a history of the applied force may be logged by memory associated with the sensor 662.

FIG. 54 illustrates a perspective expanded view of the external magnet assembly 664. Assembly 664 comprises a plate 668 and female threaded receiving post 670. Plate 668, in addition to supporting the external magnet 676, may be configured to also function as a magnetic shielding. External magnet 676 is housed in magnet housing 674 that has a threaded portion 672 configured to be received by post 670. The housing 676 may be a series of housings having incrementally variable height H. The height H may be chosen by the patient or physician to vary the force applied on the patient's sternum (e.g. a longer magnet housing would place the external magnet 676 closer to the internal magnet implanted on the patient's sternum, resulting in a larger applied loading to the sternum). The magnet may also be variably positioned within each housing 676 for micro-adjustment of the applied force.

Referring back to FIG. 53, a data-logging or storage device 680 may be coupled to the sensor 662 and mounted to the chest plate 644. The data logger 680 may be configured to receive sensor data of periodic measurements and store the data for later download and access.

It is appreciated that portions of the above embodiments may be used interchangeably with other embodiments where applicable. For example, any of the internal magnet configurations may be interchangeably used with the external magnet platforms to apply force to the internal body member of interest.

2. Scoliosis

FIGS. 18A and 18B illustrate the curvature of a normal spine 300. The spine is relatively straight in the sagittal plane 302 and has a double curve in the coronal plane 304. As shown below, the thoracic section 308 of the spine is convex posteriorly and the lumbar section 306 of the spine is convex anteriorly. Normally there should be no lateral curvature of the spine about the saggital plane 302.

Figure 19B:
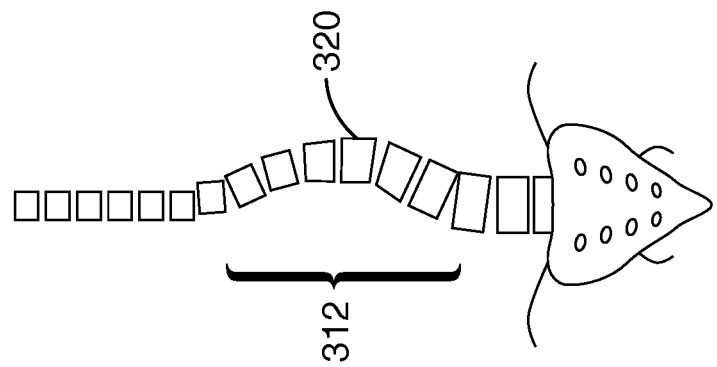
Figure 19A:
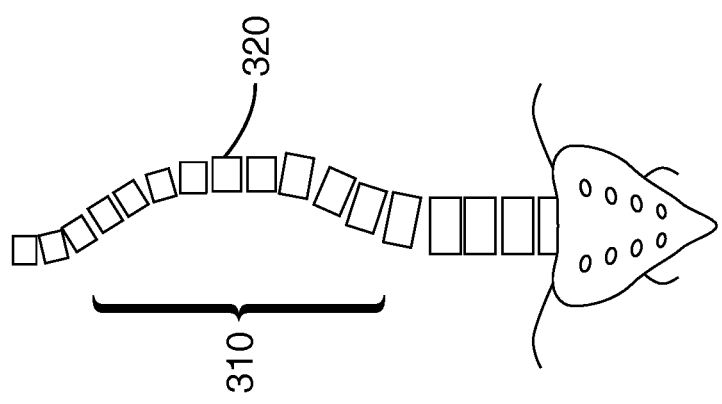
Figure 19D:
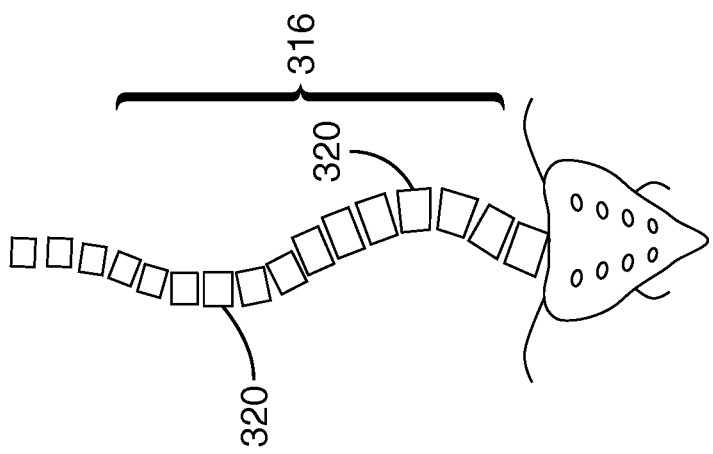
Figure 19C:
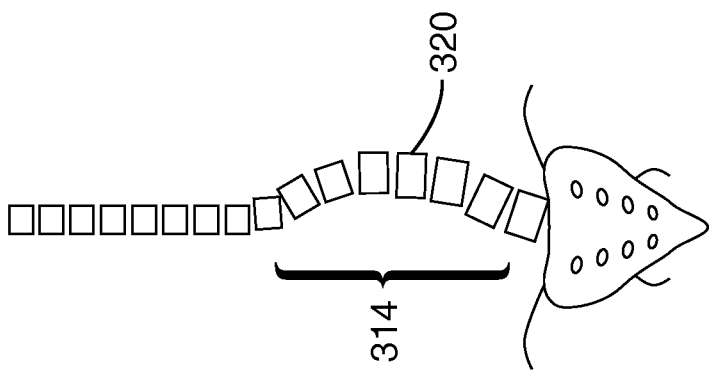

Scoliosis is a deformity that generally comprises by both lateral curvature and vertebral rotation. FIGS. 19A-D illustrate various forms of abnormal lateral curvature of the spine. FIG. 19A shows abnormal thoracic curvature 310. FIG. 19B shows abnormal thoracolumbar curvature 312. FIG. 19C shows abnormal lumbar curvature 314. Finally, some cases involve a double curvature of the spine, as shown in FIG. 19D shows abnormal thoracic curvature.

FIG. 20 illustrates rotation of the spine and corresponding effect on the rib cage 332 s a result of scoliosis. As the disease progresses, the vertebrae 330 and spinous processes in the area of the major curve rotate toward the concavity of the curve. As the vertebral bodies rotate, the spinous processes deviate more and more to the concave side and the ribs follow the rotation of the vertebrae. The posterior ribs on the convex side 336 are pushed posteriorly, causing narrowing of the thoracic cage and the characteristic rib hump seen in thoracic scoliosis. The anterior ribs on the concave side 334 are pushed laterally and anteriorly.

Now referring to FIG. 21, a schematic view of external platform 350 is illustrated with implant 340 installed on vertebrae 330 of the spine. Vertebrae 330 is preferably located at the apex 320 of the abnormal curvature shown in FIGS. 19A-D. In a preferred embodiment implant 340 is anchored to vertebrae 330 via a bone screw 336. Screw 336 may be threaded into a bore 334 in the pedicle 332 of the vertebrae according to commonly used procedures for a variety of spinal conditions, including degenerative disc disease and scoliosis. Examples of such systems are disclosed in U.S. Pat. Nos. 6,648,915; 6,010,503; 5,946,760; 5,863,293; 4,653,481, etc., the entire disclosures of which are incorporated herein by reference.

Once pedicle screw 336 is installed, internal magnet 342 may be fastened to screw 336 via magnet casing 338 and nut 346. Following the same procedure, a second internal magnet 344 may also be installed on the pedicle on the opposite side of implant 340.

After installation of implant 340, external platform 350 may be placed on the patient's back 366 adjacent to the installed implant. Platform may be retained to the torso of the patient by a strap the circles the patient's waist or chest at the elevation of the implanted vertebrae 330. Platform 350 comprises a support 352 that adjustably holds first external magnet 360. First external magnet 360 is hung inside recess 364 by a plurality rods 354, which are fastened to external mounting plate 358 housing magnet 360. The angle and height of magnet 360 may be incrementally adjusted by adjustment member 356.

As illustrated in FIG. 21, external magnet 360 and internal magnet 342 may be positioned with facing positive poles (or facing negative poles) to generate a repulsive force between the platform 350 and the implant 340. The resulting magnetic force creates a rotational moment R on the vertebrae 330 to incrementally reorient the vertebrae 330 and diminish the abnormal rotation angle β. As vertebrae 330 rotates to a more normal orientation, the rest of the vertebrae of the spine follow.

If a second internal magnet 344 is installed opposite internal magnet 342, a second external magnet 362 may be positioned opposite internal magnet 344. As shown in FIG. 1, the opposing magnets may be positioned to generate an attractive force, thereby increasing the magnitude of the rotational moment R on the vertebrae.

In addition to effecting rotation of the spine, platform 350 may be oriented to correct for lateral curvature of the spine. By placing the platform 350 to the line up to the left of the implants, as shown in FIG. 21, a translational force T is created on the vertebrae 330 as a result of the attractive force between the second external magnet 362 and second internal magnet 344. In this configuration, external magnet 360 may be removed to increase the attractive force. The platform 350 may be incrementally repositioned to continue translation of the vertebrae 330.

3. Other Applications

Variations of the above embodiments could be use to gradually correct a variety of deformities. For example, pectus carinatum (a deformity of the chest involving a sternal protrusion) may be treated with the embodiments shown in FIGS. 14-17 and orienting the magnets to apply a repulsive rather than attractive force.

In another alternative embodiment, which may be beneficial for soft tissue deformities, a magnetic force discontinuously applied in order to accommodate blood flow to the tissue. For example, the force may be applied for a period of time (e.g. a minute) and then taken off for another period of time (applied in a pulsed fashion) in order to let blood flow back to the tissue being "reformed". In one embodiment illustrated in FIG. 22, a pulsed force field is generated by rotation of the external magnet 402 with respect to fixed internal magnet 402. The magnets may have magnetized quadrants 404 that repel/attract or become neutral upon a 90 degree rotation with respect to each other to achieve tension alternating with relaxation. In an alternative embodiment, the external magnet is moved closer and then farther from the internal magnet by rotating it on a cam (not shown).

In addition to magnetic force fields configured to manipulate body members by attraction of two magnets (e.g. the device above for repair of pectus excavatum), the magnets may be configured to provide a repulsive force (e.g. a magnetic Elizeroff to lengthen bone). In the embodiment illustrated in FIG. 23, internal repulsion device 410 comprises first member 414 partially encased in second member 412, wherein first member 414 is allowed to slide inside second member 412. Each member has a corresponding internal magnet 416, 418 which are configured to repel each other, thus forcing first member 414 to separate from second member 412 to form a "magnetic spring" to distance anatomy located on ends 420 and 422. The repulsive force may be varied by adjusting the position of magnets 418 and 416 away from ends 420 and 422.

Repulsion device 410 may be used in a variety of applications where gradual force may be applied to reposition or deform one or more body members. For example, device 410 may be disposed such that ends 420 and 422 are attached to two separate locations of a bone to lengthen or alter the shape of the bone.

In an alternative embodiment illustrated in FIG. 24, repulsion device 430 may be used having reservoir 434 and pump 436. Pump 436 may be positioned underneath the patient's skin 438, such that fluid may be directed through lead line 440 to reservoir 434 in second chamber 432. The pump may be used to increase the volume of reservoir 434, thereby distancing magnet 416 away from end 420 to incrementally increase the repulsive force between 416 and 418.

In another alternative embodiment illustrated in FIG. 25, repulsion device 450 comprises a mechanical jackscrew 470. The device has a first member 452 and second member 454 that apply a repulsive force to attachment points 456 and 458 that may be attached to one or more body members. Rotary magnet coupling 468 has an internal magnet 474 under the patient's skin 476 and a corresponding external magnet 472.

The magnets are polarized such that rotation of the external magnet 472 causes a proportional rotation in internal magnet 474, which in turn rotates flexible shaft 478. Rotation of flexible shaft 478 is transferred to rotation of screw 462 located on first member 452 via worm gear 460. Nut 466 is attached to second member 454 and is threaded to screw 462 such that rotation of screw 462 causes the first member 452 to separate from 454. Additional force and separation may be achieved by further rotation of external magnet 474. Springs 464 may optionally be employed to create an additional preload between the first and second members.

FIG. 26 illustrates another alternative embodiment of a repulsion device 500 having an electric jackscrew. Control box 504 controls rotation of magnetic coupling 502. A signal is sent via wire 510 to electronics 512 to control electric motor 514, which drives rotation of screw 518 through gear reduction 516. Thus, a repulsive force may be incrementally applied to separate first member 524 from second member 522.

FIG. 49 illustrates yet another embodiment of a repulsion system 540. The system 540 includes a magnetically coupled implantable jackscrew assembly 550 that is magnetically driven by an external drive assembly 560. The jackscrew assembly 550 comprises a first member 542 and second member 544 housed within a hermetically sealed bellows 556. The first and second members 542, 544 are coupled to allow linear motion with respect to each other to apply a repulsive force to respective attachment points 552 and 554 that may be attached to one or more body members or body member locations. For example attachment point 552 may be coupled to a first vertebral body, and attachment point 554 may be coupled to a second vertebral body to allow incremental distraction of the spine segments.

The first member 542 is coupled to an internal drive coupling or rotor 562 that is radially magnetized (may also be axially magnetized in an alternative embodiment) into semi-cylindrical halves 564 and 566. The internal rotor 562 is coupled to drive shaft 558 inside end cap 568.

The external drive assembly 560 has an external drive magnet or rotor 572, also being radially magnetized into semi-cylindrical halves 574 and 576. The external rotor 572 is coupled to a high speed rotational unit 578 (e.g. hand drill or the like) that is capable of rotating magnet 572 at high rpm. The internal and external rotors are polarized such that, when the external drive assembly 560 is positioned with the external rotor 572 at an external location above the patient's skin from the internal rotor 562, rotation of the external rotor 572 causes a proportional rotation in internal rotor 562, which in turn rotates shaft 558. Shaft 558 is coupled to gear reduction unit 580 that facilitates a high ratio gear reduction (e.g. 256:1 or 500:1) to worm gear screw 546. Gear reduction unit 580 allows high speed micro-motion control of the jackscrew assembly 550 via a small input or rotational force from the external rotor 752. The gear reduction unit 580 may comprise a commercially available unit such as Spur Gearhead GS12A or Micro Harmonic Drive MHD 8, both from Maxon Precision Motors, Inc., Fall River, Mass.

Female screw thread or nut 548 is attached to second member 544 and is threaded to screw 546 such that rotation of screw 546 causes the first member 542 to separate or converge with respect to second member from 544. Additional force and separation may be achieved by further rotation of external magnet 572.

The second member 544 may optionally be spring loaded with biasing member 584 to create an additional preload between the first and second members. Biasing member 584 may provide a shock absorption component to the assembly for withstanding loading between first and second body members disposed on attachment points 552 and 554. Initial loading to separate attachment points 554 and 552 may soak up some or all of the travel of biasing member 584, depending on the spring rate. However, as the body members associated with attachments points 554 and 552 are gradually manipulated, the travel of biasing member 584 is restored.

FIG. 49 depicts a linear coil-spring design for biasing member 584, however it is contemplated that an elastomer or magnetic repulsion spring (as shown in FIG. 23) may also be used.

The jackscrew assembly 550 may also comprise a force measurement transducer 582 that measures the force applied to the attachment points 552, 554. Transducer 582 is configured to take readings of the applied force over time, and may be configured to store them locally on a memory chip or the like, or transmit force data to an external receiving unit via a wireless remote transmission such as RFID, IR or the like. Transducer 582 may also comprise deformable silicon pressure sensing device, such as the Micro Electro Mechanical Systems (MEMS) implant currently be developed by OrthoMEMS, Inc. for orthopedic sensing.

4. Fistula and Auto-Anastomosis

In many situations, it is desirable to have two segments of hollow viscera to be brought in continuity by creating a fistula between them. Strategic placement of magnets in accordance with the present invention may be used to create an auto-anastomosis, essentially a fistula, in a minimally invasive way.

The method of the present invention for performing an auto-anastomosis or a fistula would be to have one magnet in each of the two hollow viscera and let them collapse. Because the strength of attraction between the two magnets increases the closer they are together, the magnets can apply enough force over time to cause necrosis of the tissue between. If the timing is correct, the tissue just outside the crushed tissue will essentially heal together, creating a fistula. The magnet pair would then fall out into the lumen and could be retrieved or passed.

Referring to FIG. 27, a method and system 800 for performing a side-to-side anastomosis in two hollow viscera is described. According the method of the present invention, a first magnetic implant 802 is positioned in a first organ segment 806 at a region or location where anastomosis and fistula is desired.

Delivery of the magnet to the desired location in the body may be facilitated through open surgery or through a number of minimally invasive approaches. For example, standard techniques such as laparoscopy, thorascopy, fetoscopy and the like may be employed, depending on the desired location and/or procedure. In some procedures, delivery may be achieved without open surgery, e.g. via gastrointestinal or urinary tract endoscopy.

FIG. 27 illustrates delivery to a location in organ segment 806 by use of a catheter 830. Catheter 830 may have a variety of configurations currently available in the art for delivery of an implant or other device through a lumen. For example, catheter 830 may have a catheter tube 834 housing remotely retractable grippers 832. The grippers 832 may hold the magnet 802 inside retractable sheath 836 while the catheter 830 is delivered to the desired location in the lumen. The sheath 836 may then be retracted to allow the magnet 802 to be released at the location.

After placement of the first magnet, second magnetic implant 804 is delivered to a second organ section 808 in proximity to first section 806. It is appreciated that organ segments 806/808 may be separate locations in the same organ, such as two sections of bowel that are separated by an obstruction or atresia, or separate but adjacent organs, such as between a ureter and bladder, or arterial-venous fistula.

As shown in FIG. 27, implants 802 and 804 are generally ring-shaped having a centrally located aperture 810. Alternatively, implants 812 and 814, shown in FIG. 28, may be used that are disc shaped. Implants 812 and 814 may be used in situations where an obstruction can be temporarily tolerated until the fistula is created (explained in more detail below). The implants are generally comprised of a magnetically charged material. A coating or hermetically sealed casing, such as titanium or epoxy, may encapsulate the implants to ensure biocompatibility. The outside diameter do of the implant may vary according to the size of the desired fistula. Accordingly, the inside diameter di may vary depending on the size of the temporary passage (described in further detail below). It is also appreciated that the implant may be configured to have one of a number of shapes depending on the application, e.g. the outer and inner edges may be elliptical, or other shape to accommodate the desired fistula.

Referring now to FIG. 29, the implants 802, 804 are placed with opposite poles facing each other at the desired location for the fistula. This creates an attractive force between the magnets 802 and 804, and the interior walls 816 and 818 between the magnets. The attractive force also acts to concentrically align magnets 802 and 804 along the same axis.

As illustrated in FIG. 30, the attractive force of the magnets 802 and 804 draws the inner walls 816 and 818 together until they contact each other. A compressive force is generated on the tissue 820 of walls 816 and 818 between the magnets. This compressive force gradually increases as the magnets get closure to each other.

Referring now to FIG. 31 In situations where a temporary passage for the contents of the viscera is desired or required (e.g. an obstruction downstream from the implant location) a cutout 822 may be performed in the tissue 820 of walls 816 and 818. The cutout may be circular to generally match the shape of hole 810 of the magnets. As shown in FIG. 31, cutout 822 and holes 810 in the magnets allow flow F of the contents of the viscera to be immediately restored to essentially bypass any downstream obstruction. Cutout 822 may be made non-invasively via a cutting tool (not shown) disposed at the location via and catheter 830 (shown in FIG. 27).

Alternatively, disc-shaped magnets 812 and 814 may be used where obstruction (or other condition) of the viscera is tolerable for the period it takes to achieve auto-anastomosis. In this case, no cutout is made in walls 820.

In either case, the compressive force placed on the tissue 820 trapped between the magnets causes necrosis of the tissue 820. As shown in FIG. 32, the tissue eventually falls out over a period of time (usually within days), and the walls 816 and 818 heal, or fuse together to form a fistula 826 around the perimeter of the magnets 802/804.

Finally in FIG. 33, the magnets 802/804 and necrosed tissue between them (if any), fall out from the fistula 826 and may either be retrieved, or simply pass out of the patient's system through the newly anastomosed lumen.

The above described method and system for auto-anastomosis may be performed on any hollow viscera, lumen, organ, etc. in the body where anastomosis and/or fistula are conventionally performed. For example the system 800 may be used for side-to-side anastomosis in the vascular system, e.g. an arterial-venous fistula for vascular access.

However, the methods and system 800 are ideally suited in regions of the body that are more susceptible to necrosis under high pressure, such as the gastrointestinal and urinary tracts.

Referring to FIG. 34 of the gastrointestinal tract, the system 800 may be used to achieve anastomosis in the esophagus 840, down to the stomach 842, small intestine 846 and colon 848. For example, the anastomosis may be performed in bariatric procedures such as gastric bypass.

In addition, system 800 may be used for palliative procedures for bowel stenosis or obstruction, i.e. intestinal atresia. Intestinal atresia may occur in a number of places in the gastrointestinal tract, e.g. the duodenum 844, jejunum 850 and ileum 852 of the small intestine 846, and colon 848. An anastomosis/fistula may be readily performed in this regions given the characteristics of the bowel, and the ease of placing segments of these organs adjacent to each other to bypass an obstruction. In certain types of jejunoileal atresia, where significant portions of the small intestine are missing, the present invention may be configured to stretch the separated intestinal lumens prior to anastomosis, similar to the system disclosed in co-pending U.S. application Ser. No. 11/222,517, incorporated herein by reference in its entirety.

FIG. 35 illustrates a schematic diagram of a patient having duodenal atresia. The duodenum 844 has a blockage 858 separating an upper portion 854 from a lower portion 856 of the duodenum.

Referring now to FIG. 36, magnetic implants 802 and 804 are delivered separately to each side of the blockage or atresia 858. This may be achieved via separate catheters, similar to catheter assembly 830, into the adjacent regions. For example, magnet 802 may be delivered via a catheter through the mouth and esophagus, or via laparoscopy. Magnet 804 may also be delivered via laparoscopy, or via endoscope. The magnets are positioned, and the segments 854 and/or 856 are maneuvered so that the magnets align adjacent to each other across the tissue of each segment. The auto-anastomosis process, as depicted in FIGS. 30-33, occurs over a period of time until a fistula is achieved and the magnets dislodge to be retrieved or pass out of the system.

Referring now to FIG. 37, system 800 may also be implemented to perform an anastomosis/fistula in the organs of the urinary tract, including urethra 866, bladder 864, and ureters 860. For example, implants 802 and 804 may be delivered to appropriate locations to create a fistula between a ureter and the bladder, or in the renal pelvis 870.

Referring now to FIGS. 38-39, system 880 may be implemented to create an ostomy. As shown in FIG. 38, a magnetic implant 882 may be delivered to a desired location in the organ 886 to be treated, e.g. the colon for a colostomy, small intestine for an illeostomy, or ureter for a urostomy. The implant 882 may be delivered via catheter 830 either by endoscope or laparoscope. An external magnet 884 is then placed over the patient's skin 888 adjacent the internal magnet 882, with opposite polarities facing each other so that an attractive force is generated between the magnets.

The attractive force between magnets 882 and 884 generates a compressive force on the tissue in between them, e.g. visceral wall 894, abdominal wall 890, and skin 888. This compressive force causes the tissues to necrose, and eventually anastomose until the magnets and tissue fall out, creating a fistula and stoma 892 through the visceral wall, abdominal wall and skin, as illustrated in FIG. 39. A plastic pouch, e.g. colostomy bag, is then attached to the skin 888 around stoma 892.

As shown in FIG. 40, the system may also include one or more intermediate internal magnets 896 to better facilitate necrosis of the abdominal wall 890. For example, the first implant 882 may be inserted into the desired organ 886, and a second implant 896 may be implanted in the abdominal wall between the skin 888 and visceral wall 8894. The polarities of magnets 882, 894 and 884 are aligned so that all three magnets attract toward each other. This has the effect of shortening the distance between magnets, thereby increasing the compressive force between them to facilitate necrosis and auto-anastomosis. Two or more intermediate internal magnets may also be used where necessary.

All magnetic members or implants heretofore disclosed may have magnetic, ferromagnetic, or electromagnetic properties and may include one or more materials, e.g. magnetic or non-magnetic.

Referring now to FIG. 41, magnetic implants 900 and 902 incorporating curvilinear surfaces may be positioned at two sections of a lumen or two adjacent lumens. These implants may be used to generate a variable force across a section of tissue, as described in further detail below. Implants 900 and 902 may be solid, or have a central lumen 910 to be used in situations where an obstruction can be temporarily tolerated until the fistula is created.

The implants 900, 902 are placed with opposite poles facing each other at the desired location in lumen sections 806, 808 for generating the fistula.

This creates an attractive force between the magnets 900 and 902, and the interior walls 816 and 818 between the magnets. The attractive force also acts to concentrically align magnets 900 and 902 along the same axis 912.

As illustrated in FIG. 42, the attractive force of the magnets 900 and 902 draws the inner walls 816 and 818 together until they contact each other. A compressive force is generated on the tissue 820 of walls 816 and 818 between the magnets. This compressive force gradually increases as the magnets get closure to each other.

As shown in FIG. 41, the first magnet 900 comprises a concave or cupped surface 904 having a radius $r_c$, while the second magnet 902 of opposite polarity, comprises a convex or spherical surface 906 having a radius $r_s$. In a preferred embodiment, the cupped surface 904 has a larger radius $r_c$ than the radius $r_s$ of the convex surface 906 of magnet 902, i.e. $r_c > r_s$.

The differing radii of magnets 900 and 902 results in a non-uniform force distribution P across the surfaces of the magnets. As illustrated in FIG. 43 (showing only magnet 900 for clarity), the force distribution P across the magnet surface 904 is highest along the central axis 912, where the magnets are at their closest. Moving radially outward toward the perimeter of the magnet, the force becomes increasingly smaller, until reaching the smallest force at the perimeter 908, where the magnets 900 and 902 are furthest from each other.

The non-uniform stress distribution as shown in FIGS. 41-43 is advantageous for auto-anastomosis of tissue. The larger force along central axis 912 can be configured to be strong enough to generate necrosis of tissue 820 in that region. Correspondingly, the smaller force at the perimeter will be just large enough to fuse the tissue 820 on the periphery, while still promoting growth. Thus, the tissue in the center is necrosed to generate the aperture, while the tissue in the periphery is still live, facilitating a robust fusion between walls 816 and 818.

Referring now to FIG. 44 the necrosed tissue at the center of the compressed tissue 820 falls out, forming a temporary passage 822 for the contents of the viscera to flow from lumen section 806 through of hole 810 of the magnets, to lumen 808. As described above with respect to FIG. 31, a cutout may be performed where the contents of the viscera are to be immediately restored to essentially bypass any downstream obstruction.

As shown in FIG. 45, more of the centrally-located tissue eventually falls out over a period of time (usually within days), allowing the magnets 900, and 902 to pass the fistula and pass out the body or be retrieved. The walls 816 and 818 heal and fuse together at 820 a fistula 826.

The magnets 900 and 902 are shown in FIGS. 41-45 above as having one curvilinear surface each. However, as shown in FIG. 46, magnet 918 may have two concave surfaces 922, and magnet 920 may have a generally spherical outer surface 924 to form a sphere. In this configuration, the opposing-charged magnets will be assured to line up properly to the correct surface.

FIG. 47 illustrates an exploded view of a convex magnet assembly 930 and concave magnet assembly 940. The convex magnet assembly comprises a ring magnet 938 that is configured to be inserted into recess 936 in casing 932. The casing 932 comprises a convex or spherical surface 934 that may be a non-magnetic material, such as Teflon, or other polymer. Concave magnet assembly 940 comprises a corresponding ring magnet 948 of opposite polarity, which is configured to be inserted into recess 946 of casing 942. The casing has a cupped or concave surface 944 that preferably has a larger radius than spherical surface 934.

FIG. 48 illustrates magnet assemblies 930 and 940 installed in opposing lumen sections. The attractive force of magnets 938 and 948 compress the tissue of walls 816 and 818 disposed between the magnet casings 932, 942. Although the magnets generate a constant force across their circumference, the varying radii of cupped surface 944 and spherical surface 934 compress the tissue of walls 816 and 818 non-uniformly across the circumference of the assemblies. As shown in FIG. 48, the tissue at the central axis 912 is more compressed than at the periphery 908. Thus, the tissue in the center is necrosed to generate the aperture, while the tissue in the periphery is still live, facilitating a robust fusion between walls 816 and 818.

The above described method and system for auto-anastomosis may be performed on any hollow viscera, lumen, organ, etc. in the body where anastomosis and/or fistula are conventionally performed. For example the system 800 may be used for side-to-side anastomosis in the vascular system, e.g. an arterial-venous fistula for vascular access, or gastrointestinal and urinary tracts.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A body member repulsion device, comprising:
    a. a jackscrew capable of being implanted to a body, wherein said jackscrew comprises a first attachment point capable of attaching to a first member and a second attachment point capable of attaching to a second member;
    b. a biasing member configured to absorb loading between said first member and said second member;
    c. an internal rotary magnet coupler capable of being implanted to said body;
    d. a work conduit, wherein said work conduit is disposed between said internal rotary magnet coupler and said jackscrew;
    e. an external rotary magnet coupler capable of being disposed outside said body and proximal to said internal rotary magnet coupler, wherein said external magnetic coupler is magnetically coupled to said internal magnetic coupler, wherein when work is applied to said external rotary magnet coupler said internal rotary magnet coupler receives said work and conveys said work to said jackscrew through said work conduit, wherein said work applied to said jackscrew moves said first attachment point and said second attachment point, or wherein said work applied to said jackscrew moves said first attachment point or said second attachment point; and
    f. a gear reduction unit coupled between said internal rotary magnet coupler and said jackscrew to allow a smaller input force on said internal rotary magnet to drive a large output force between said first and second attachments points of said jackscrew.

2. The body member repulsion device of claim 1, wherein said work conduit comprises a flexible shaft.

3. The body member repulsion device of claim 2, wherein said wherein said flexible shaft is connected to a worm drive disposed in said jackscrew.

4. The body member repulsion device of claim 1, wherein said internal magnetic coupler comprises an internal magnet.

5. The body member repulsion device of claim 1, wherein said external magnetic coupler comprises an external magnet.

* * * * *